(12) United States Patent
Yoshinari et al.

(10) Patent No.: US 9,760,219 B2
(45) Date of Patent: Sep. 12, 2017

(54) BLACK RESIN FILM, CAPACITANCE TYPE INPUT DEVICE, METHOD FOR PRODUCING THEM, AND IMAGE DISPLAY APPARATUS USING THE SAME

(71) Applicant: FUJIFILM Corporation, Minato-ku, Tokyo (JP)

(72) Inventors: Shinichi Yoshinari, Fujinomiya (JP); Hitoshi Namikawa, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 393 days.

(21) Appl. No.: 14/499,633

(22) Filed: Sep. 29, 2014

(65) Prior Publication Data
US 2015/0015813 A1   Jan. 15, 2015

Related U.S. Application Data

(63) Continuation of application No. PCT/JP2013/057483, filed on Mar. 15, 2013.

(30) Foreign Application Priority Data

Mar. 30, 2012  (JP) .................................. 2012-078946

(51) Int. Cl.
   *G06F 3/044* (2006.01)
   *C07D 251/24* (2006.01)
   (Continued)

(52) U.S. Cl.
   CPC ........... *G06F 3/044* (2013.01); *C07D 251/24* (2013.01); *G03F 7/027* (2013.01); *G03F 7/031* (2013.01);
   (Continued)

(58) Field of Classification Search
   CPC ....... C07D 251/24; G03F 7/027; G03F 7/031; G03F 7/105; G03F 7/2024; G03F 7/40; G06F 1/1692; G06F 3/044
   (Continued)

(56) References Cited

U.S. PATENT DOCUMENTS

| 5,821,016 A | * 10/1998 | Satoh | .................... G02B 5/223 |
| | | | 430/287.1 |
| 7,796,124 B2 | 9/2010 | Sato et al. | |

(Continued)

FOREIGN PATENT DOCUMENTS

| CN | 1955904 A | 5/2007 |
| CN | 101657414 A | 2/2010 |

(Continued)

OTHER PUBLICATIONS

Office Action dated May 24, 2016 from the Taiwanese Intellectual Property Office in counterpart Taiwanese Application No. 102109264.

(Continued)

*Primary Examiner* — Dmitriy Bolotin
(74) *Attorney, Agent, or Firm* — Sughrue Mion, PLLC

(57) ABSTRACT

A black resin film is produced by applying a photosensitive resin composition containing a black pigment, an alkali-soluble polymer compound, an ethylenic unsaturated bond-containing compound and α-aminoalkylphenone or α-hydroxyalkylphenone as a photopolymerization initiator, to a substrate; and subjecting the composition to exposure, development and post-exposure. The post-exposure is performed from both side with 1,300 mJ/cm² or more in terms of i line.

13 Claims, 5 Drawing Sheets

(51) Int. Cl.
*G03F 7/031* (2006.01)
*G03F 7/40* (2006.01)
*G03F 7/027* (2006.01)
*G03F 7/105* (2006.01)
*G03F 7/20* (2006.01)
*G06F 1/16* (2006.01)

(52) U.S. Cl.
CPC ............ *G03F 7/105* (2013.01); *G03F 7/2024* (2013.01); *G03F 7/40* (2013.01); *G06F 1/1692* (2013.01)

(58) Field of Classification Search
USPC .............................. 349/12; 430/18, 319, 325
See application file for complete search history.

(56) References Cited

U.S. PATENT DOCUMENTS

| | | | |
|---|---|---|---|
| 8,665,226 | B2 | 3/2014 | Liu et al. |
| 8,823,653 | B2 | 9/2014 | Matsuo |
| 2005/0095529 | A1* | 5/2005 | Sugasaki ............... B41C 1/1008 430/270.1 |
| 2007/0165006 | A1 | 7/2007 | Sato et al. |
| 2008/0309635 | A1 | 12/2008 | Matsuo |
| 2009/0009695 | A1* | 1/2009 | Ito ......................... G02B 5/201 349/96 |
| 2009/0029285 | A1* | 1/2009 | Nakazto ................ G03F 7/2018 430/270.1 |
| 2009/0207151 | A1 | 8/2009 | Liu et al. |
| 2010/0072889 | A1* | 3/2010 | Takahashi ................ C08F 2/50 313/504 |
| 2010/0075237 | A1* | 3/2010 | Ishizeki ................ G03F 7/0388 430/7 |
| 2010/0253888 | A1* | 10/2010 | Tanaka .................. G03F 7/0007 349/106 |
| 2011/0123929 | A1 | 5/2011 | Fujita et al. |
| 2012/0162130 | A1 | 6/2012 | Liu et al. |
| 2013/0038571 | A1* | 2/2013 | Ho ......................... G06F 3/044 345/174 |
| 2013/0141385 | A1 | 6/2013 | Liu et al. |
| 2013/0141386 | A1 | 6/2013 | Liu et al. |
| 2014/0231729 | A1* | 8/2014 | Shiota .................... G02B 5/223 252/586 |
| 2015/0092123 | A1* | 4/2015 | Gotoh ..................... B32B 27/20 349/12 |

FOREIGN PATENT DOCUMENTS

| | | |
|---|---|---|
| CN | 101680983 A | 3/2010 |
| JP | 10-282650 A | 10/1998 |
| JP | 2002-023359 A | 1/2002 |
| JP | 2007-122326 A | 5/2007 |
| JP | 2008-134583 A | 6/2008 |
| JP | 2009-193587 A | 8/2009 |
| JP | 2010-097210 A | 4/2010 |
| JP | 4506785 B2 | 7/2010 |
| JP | 2011-095716 A | 5/2011 |
| JP | 2011-194799 A | 10/2011 |
| WO | 2008/090640 A1 | 7/2008 |

OTHER PUBLICATIONS

Office Action dated Apr. 19, 2016 from the Korean Intellectual Property Office in counterpart Korean Application No. 10-2014-7028878.
Office Action dated Oct. 26, 2016, issued by the Korean Intellectual Property Office in corresponding Korean Application No. 10-2014-7028878.
Office Action dated Mar. 3, 2015, issued by the Japanese Patent Office in corresponding Japanese Application No. 2013-053974.
International Preliminary Report on Patentability issued on Oct. 9, 2014 by the International Bureau of WIPO in counterpart International Application No. PCT/JP2013/057483.
Written Opinion dated Apr. 16, 2013 from the International Bureau of WIPO in corresponding International Application No. PCT/JP2013/057483.
International Search Report for PCT/JP2013/057483 dated Jun. 18, 2013.
Office Action dated Jun. 16, 2017 from the State Intellectual Property Office of the P.R.C. in counterpart Chinese Application No. 201380017364.4.

* cited by examiner

BLACK RESIN FILM, CAPACITANCE TYPE INPUT DEVICE, METHOD FOR PRODUCING THEM, AND IMAGE DISPLAY APPARATUS USING THE SAME

CROSS-REFERENCE TO RELATED APPLICATIONS

This application is a continuation application of International Application No. PCT/JP2013/057483, filed Mar. 15, 2013, which in turn claims the benefit of priority from Japanese Application No. 2012-078946, filed Mar. 30, 2012, the disclosures of which Applications are incorporated by reference herein in their entirety.

BACKGROUND OF THE INVENTION

Field of the Invention

The present invention relates to a black resin film (i.e., a decorative material) that has a high bulk strength after heating even when it has a high optical density by using a black pigment, a method for producing the same, a method for producing a capacitance type input device that contains the black resin film and is capable of detecting a touch position of a finger as a change of capacitance, a capacitance type input device obtained by the production method, and an image display apparatus equipped with the capacitance type input device as a constitutional component.

Background Art

In recent years, electronic equipments, such as mobile telephones, car navigation systems, personal computers, ticket vending machines and banking terminals, include ones that are equipped with a tablet type input device on a surface of a liquid crystal display device or the like, in which an indicating image is displayed on an image display region of the liquid crystal display device, and the position where the indicating image is displayed is touched with a finger, a stylus pen or the like by referring to the indicating image, thereby enabling input of information corresponding to the indicating image.

The input device (i.e., a touch-sensitive panel) includes a resistive film type, a capacitance type and the like. However, the resistive film type input device has a two-layer structure containing a film and a glass plate, in which the film is pressed down to short-circuit them, and thus has disadvantages including the narrow operative temperature range and the time-lapse deterioration.

On the other hand, the capacitance input device has such an advantage that a translucent conductive film may be simply formed on a single substrate. The capacitance input device includes, for example, such a type that has electrode patterns that extend to cross each other, and on touching the electrodes with a finger or the like, the change of the capacitance between the electrodes is detected to determine the input position (see, for example, Patent Literature 1).

The capacitance input device also includes such a type that alternating currents having the same phase and the same potential are applied to both ends of the translucent conductive film, and on forming a capacitor by touching with a finger or bringing a finger close thereto, a weak electric current flowing is detected to determine the input position. As the capacitance type input device of this type, such a capacitance type input device is disclosed that contains plural first transparent electrode patterns formed of plural pad portions formed to extend in a first direction and connected through connecting portions, and plural second transparent electrode patterns electrically insulated from the first transparent electrode patterns with an interlayer insulating layer, and formed of plural pad portions formed to extend in a direction intersecting the first direction (see, for example, Patent Literature 2).

A capacitance type touch-sensitive panel containing a front plate having on a non-contact surface thereof a mask layer (which is preferably a black layer or a black resist), a sensor circuit containing a metal trace, and an interlayer insulating layer, which are integrated, is disclosed (see, for example, Patent Literature 3). In this literature, the black layer is disposed to cover and hide the metal trace for transferring signals, so as to prevent the metal trace from being exposed on viewing the substrate or the lens from the above, and thus used as a decorative material for enhancing the appearance of the substrate or the lens. Patent Literature 3 describes that the capacitance type touch-sensitive panel may be reduced in thickness and weight since the front plate is integrated with the capacitance type input device, but does not describe details of the production method, such as the composition of the mask layer, particularly the composition of the decorative material, which is a black layer.

In a circuit of an FPS (flexible printed circuit board), such as a sensor circuit containing a metal trace, generally, a mask layer is provided as a resist using a photosensitive resin composition. As the resist for FPS, for example, the etching resist material described in Patent Literature 4 may be used, and a resist having a target shape may be obtained through exposure and development. Patent Literature 4 describes that the use of a photosensitive resin composition containing an alkali-soluble acrylic resin, a urethane monomer and a particular photopolymerization initiator provides a photosensitive element that has high sensitivity with a low exposure amount and is excellent in adhesion and tent film strength, but fails to describe a photosensitive resin composition containing a black pigment.

Patent Literature 5 describes that the use of a black photosensitive resin composition formed of an alkali-soluble acrylic resin material, a particular crosslinking agent, a photo acid generator and a black pigment, as a shielding film for a color filter may provide a color filter having a black matrix that has a density sufficient for shielding light, has less surface roughness and a high film density, and is free of pattern defects. Patent Literature 5 describes as the crosslinking agent only a methylolated urea, a urea resin, a methylolated melamine, a butylolated melamine, a methylolated guanamine, and alkyl ethers thereof, and in the examples, Nikalac MW-30M (produced by Sanwa Chemical Co., Ltd.) having no acryloyl group but having only an N-methylol group is used, but there is no description of a compound containing an ethylenic unsaturated bond. Patent Literature 5 uses a photo acid generator, but does not describe a photopolymerization initiator.

CITATION LIST

Patent Literatures

Patent Literature 1: JP-A-2007-122326
Patent Literature 2: Japanese Patent No. 4,506,785
Patent Literature 3: JP-A-2009-193587
Patent Literature 4: JP-A-2002-23359
Patent Literature 5: JP-A-10-282650

SUMMARY OF INVENTION

However, when the present inventors have produced a decorative material by producing a black resist by adding a black pigment to the photosensitive resin composition described in Patent Literature 4, it has been found that there are such a problem that sufficient exposure is difficult to be performed when adding a black pigment, and the bulk strength after exposure and development, and then after heating to 240° C. for 80 minutes and further heating to 300° C. for 30 minutes is deteriorated.

When the present inventors have produced a decorative material by using the black photosensitive resin composition described in Patent Literature 5, it has been found that there are such a problem that the bulk strength of the black photosensitive resin composition described in Patent Literature 5 after exposure and development, and then heating to 240° C. for 80 minutes and further heating to 300° C. for 30 minutes is also deteriorated.

When the black resin film has a low bulk strength, a circuit attached to the decorative black film for connecting a circuit outside a touch-sensitive panel and the touch-sensitive panel may be dismounted on application of an excessive force, which may leads reduction in reliability.

A problem to be solved by the invention is to provide a black resin film that has a high bulk strength after heating even when a high optical density is achieved by using a black pigment, and a method for producing the same.

The inventors have found that by subjecting a photocurable resin composition containing a black pigment having a particular composition to post-exposure in addition to exposure and development, such a black resin film may be provided that has a high bulk strength after heating even when a high optical density is achieved by using a black pigment.

The invention as specific measures for solving the problem is as follows.

[1] A black resin film containing a black pigment, an alkali-soluble polymer compound, an ethylenic unsaturated bond-containing compound and a photopolymerization initiator, having a bulk strength after heating to 240° C. for 80 minutes and further heating to 300° C. for 30 minutes of 100 N per 1.6 mm in diameter or more.

[2] The black resin film according to the item [1], which preferably has a thickness of from 1.5 to 5.0 μm.

[3] The black resin film according to the item [1] or [2], which preferably has a thermal weight reduction rate after heating to 240° C. for 80 minutes and further heating to 300° C. for 30 minutes of 39.2% or less.

[4] The black resin film according to any one of the items [1] to [3], wherein the photopolymerization initiator is preferably an α-aminoalkylphenone compound or an α-hydroxyalkylphenone compound.

[5] The black resin film according to any one of the items [1] to [4], which preferably has a taper angle on a side surface thereof that satisfies the following expression (1) and the following expression (2):

$$\Theta_1 \leq 40°$$  Expression (1)

wherein $\Theta_1$ represents an angle that is 90° or less among angles formed between a straight line $l_{12}$ and an extended line $l_A$ of a bottom surface of the black resin film, the straight line $l_{12}$ passing through an intersecting point $C_1$ and an intersecting point $C_2$, the intersecting point $C_1$ being an intersecting point of a side surface of the black resin film and a straight line at a 1/4 height from a surface of the black resin film on a side of a substrate when a height of the black resin film is divided into four equal parts, the intersecting point $C_2$ being an intersecting point of the side surface of the black resin film and a straight line at a 2/4 height from the surface of the black resin film on the side of the substrate when the height of the black resin film is divided into four equal parts, $$\Theta_2 \leq 40°$$  Expression (2)

wherein $\Theta_2$ represents an angle that is 90° or less among angles formed between a straight line $l_{23}$ and an extended line $l_B$ of a portion of a top surface of the black resin film that is approximately in parallel to the bottom surface of the black resin film, the straight line $l_{23}$ passing through an intersecting point $C_2$ and an intersecting point $C_3$, the intersecting point $C_2$ being an intersecting point of the side surface of the black resin film and a straight line at a 2/4 height from the surface of the black resin film on the side of the substrate when the height of the black resin film is divided into four equal parts, the intersecting point $C_3$ being an intersecting point of the side surface of the black resin film and a straight line at a 3/4 height from the surface of the black resin film on the side of the substrate when the height of the black resin film is divided into four equal parts.

[6] The black resin film according to any one of the items [1] to [5], which preferably further contains a solvent.

[7] The black resin film according to the item [6], which preferably contains, as the solvent, a first solvent that has an evaporation rate of 200% or more of butyl acetate and a second solvent that has an evaporation rate of 50% or less of butyl acetate.

[8] The black resin film according to the item [6] or [7], which preferably contains, as the solvent, a solvent that is a polyhydric alcohol derivative and a solvent that is a ketone.

[9] A method for producing a black resin film, containing applying a photosensitive resin composition containing a black pigment, an alkali-soluble polymer compound, an ethylenic unsaturated bond-containing compound and a photopolymerization initiator, to a substrate, exposing the photosensitive resin composition on the substrate, developing the photosensitive resin composition thus exposed, and performing post-exposure after the development, and satisfying the following condition (A) or the following condition (B):

Condition (A): the photopolymerization initiator is an α-aminoalkylphenone compound or an α-hydroxyalkylphenone compound, and Condition (B): the post-exposure after the development is performed from both a surface of the photosensitive composition on a side that is in contact with the substrate and a surface thereof on a side that is not in contact with the substrate.

[10] The method for producing a black resin film according to the item [9], wherein an exposure amount in the post-exposure after the development is preferably 1,300 mJ/cm² or more in terms of i line.

[11] The method for producing a black resin film according to the item [10], wherein the substrate is preferably a transparent substrate.

[12] The method for producing a black resin film according to the item [11], wherein the transparent substrate is preferably an insulating transparent substrate.

[13] The method for producing a black resin film according to any one of the items [9] to [12], which preferably satisfies both the condition (A) and the condition (B).

[14] The method for producing a black resin film according to any one of the items [9] to [13], the photosensitive resin composition is preferably transferred from a photosensitive transfer film, which contains a provisional support having accumulated thereon the photosensitive resin composition, to the substrate.

[15] A black resin film that is produced by the method for producing a black resin film according to any one of the items [9] to [14].

[16] A decorative material for a capacitance type input device, containing the black resin film according to any one of the items [1] to [8] and [15].

[17] A capacitance type input device containing the decorative material for a capacitance type input device according to the item [16].

[18] A method for producing a capacitance type input device containing a front plate and on a non-contact surface of the front plate at least the following components (1) to (4), the component (1) being produced by the method for producing a black resin film according to any one of the items [9] to [14]:

(1) a decorative material, (2) plural first transparent electrode patterns that contain plural pad portions that are formed to extend in a first direction and connected through connecting portions, (3) plural second electrode patterns that are electrically insulated from the first transparent electrode patterns, and contain plural pad portions that are formed to extend in a direction intersecting the first direction, and (4) an insulating layer that electrically insulates the first transparent electrode patterns and the second electrode patterns from each other.

[19] The method for producing a capacitance type input device according to the item [18], wherein the capacitance type input device further contains (5) a conductive element that is other than the first transparent electrode patterns and the second electrode patterns and is electrically connected to at least one of the first transparent electrode patterns and the second electrode patterns.

[20] The method for producing a capacitance type input device according to the item [18] or [19], wherein the second electrode patterns are transparent electrode patterns.

[21] A capacitance type input device that is produced by the method for producing a capacitance type input device according to any one of the items [18] to [20].

[22] An image display apparatus containing the capacitance type input device according to the item [17] or [21] as a constitutional component.

According to the invention, there may be provided a black resin film that has a high bulk strength after heating even when a high optical density is achieved by using a black pigment, and a method for producing the same.

DESCRIPTION OF EMBODIMENTS

Figure 1:
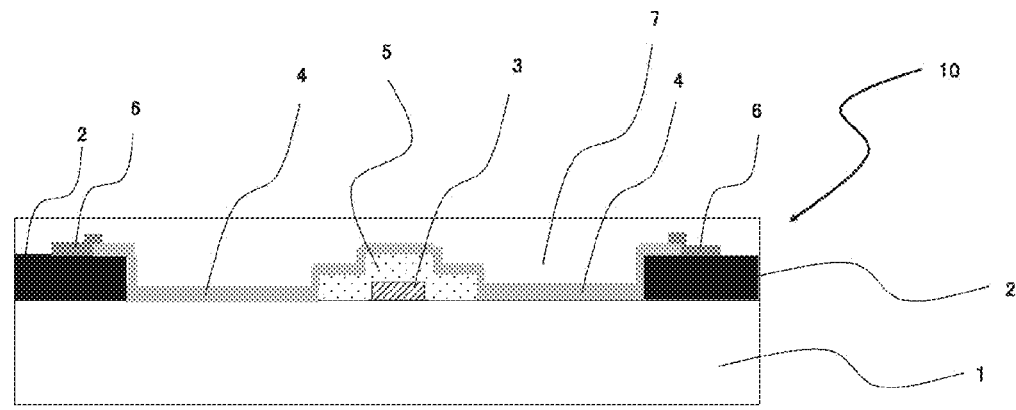
FIG. 1 is a cross sectional view showing a structure of a capacitance type input device according to the invention.

The black resin film of the invention (i.e., the decorative material for a capacitance type input device of the invention) and the method for producing the same, the method for producing a capacitance type input device, the capacitance type input device and the image display apparatus, according to the invention will be described below.

Black Resin Film

The black resin film of the invention contains a black pigment, an alkali-soluble polymer compound, an ethylenic unsaturated bond-containing compound and a photopolymerization initiator, and has a bulk strength after heating to 240° C. for 80 minutes and further heating to 300° C. for 30 minutes of 100 N per 1.6 mm in diameter or more.

According to the constitution, the black resin film may have a high bulk strength after heating even when a high optical density is achieved by using a black pigment.

The composition, characteristics and shape of the black resin film of the invention, and the method for producing the black resin film of the invention will be described below.

Composition

The black resin film of the invention contains a black pigment, an alkali-soluble polymer compound, an ethylenic unsaturated bond-containing compound and a photopolymerization initiator.

Black Pigment

The black pigment used in the black resin film of the invention is not particularly limited unless it deviates from the substance of the invention. The black resin film of the invention preferably has an optical density of 2.0 or more, more preferably 2.5 or more, and particularly preferably 2.8 or more. When the optical density is less than 2.0, there is a possibility of causing light leakage in a display device.

As the black pigment used in the invention, known black pigments (including an organic pigment, an inorganic pigment, a dye and the like) may be preferably used. In the invention, mixtures of pigments of red, blue, green and the like may be used in addition to the black pigment.

The optical density may be measured with a transmission densitometer, BMT-1, produced by Sakata Inx Engineering Co., Ltd.

Examples of the black pigment include carbon black, titanium carbide, iron oxide, titanium oxide and graphite, and among these, carbon black is preferred.

The black pigment (preferably carbon black) is preferably used in the form of a dispersion liquid. The dispersion liquid may be prepared by adding and dispersing a composition, which is obtained by mixing the black pigment and a pigment dispersant in advance, in an organic solvent (or a vehicle) described later. The vehicle herein means a portion of a medium, in which a pigment is dispersed, when a paint is in the form of liquid, and the vehicle is in the form of liquid and contains a component that is combined with the black pigment to form a coated film (i.e., a binder) and a component that dissolves and dilutes the binder (i.e., an organic solvent).

The dispersing machine used for dispersing the black pigment is not particularly limited, and examples thereof include known dispersing machine, such as a kneader, a roll mill, an attritor, a super mill, a dissolver, a homomixer and a sand mill, described, for example, in K. Asakura, "Ganryo no Jiten" (Encyclopedia of Pigments), 1st ed., Item 438, Asakura Publishing Co., Ltd. (2000). The black pigment may also be finely pulverized through mechanical grinding described in the same literature, page 310.

A black pigment that is used in the invention preferably has a number average particle diameter of from 0.001 to 0.1 μm, and more preferably from 0.01 to 0.08 μm. The term "particle diameter" herein means the diameter of the circle that has the same area as that of the electron micrograph, and the term "number average particle diameter" means such a value that the particle diameter is measured for many particles, and the average value of 100 particles is obtained.

Alkali-Soluble Polymer Compound

Examples of the alkali-soluble polymer compound used include the polymers described in the paragraph [0025] of JP-A-2011-95716 and the paragraphs [0033] to [0052] of JP-A-2010-237589. In the invention, a random copolymer of benzyl methacrylate and methacrylic acid is preferably used.

Ethylenic Unsaturated Bond-Containing Compound

Examples of the ethylenic unsaturated bond-containing compound used include the polymerizable compounds described in the paragraphs [0023] to [0024] of Japanese Patent No. 4,098,550. In the invention, DPHA (dipentaerythritol hexaacrylate) is preferably used.

Photopolymerization Initiator

Examples of the photopolymerization initiator used include the polymerizable compound described in the paragraphs [0031] to [0042] of JP-A-2011-95716.

Preferred examples among these include an α-aminoalkylphenone compound, an α-hydroxyalkylphenone compound, a trichloromethyltriazine compound and an oxime ester compound.

In the black resin film of the invention, the photopolymerization initiator is preferably an α-aminoalkylphenone compound or an α-hydroxyalkylphenone compound from the standpoint of enhancing the bulk strength after heating.

The mass ratio of the photopolymerization initiator with respect to the ethylenic unsaturated bond-containing compound in the black resin film of the invention is preferably from 0.05 to 0.125 from the standpoint of the taper angle and the prevention of deposition, and is more preferably from 0.070 to 0.100.

Additive

The black resin film of the invention may further contain an additive. Examples of the additive include the surfactants described in the paragraph [0017] of Japanese Patent No. 4,502,784 and the paragraphs [0060] to [0071] of JP-A-2009-237362, the thermal polymerization inhibitors described in the paragraph [0018] of Japanese Patent No. 4,502,784, and the additives described in the paragraphs [0058] to [0071] of JP-A-2000-310706.

Solvent

The black resin film of the invention preferably further contains a solvent.

Examples of the solvent that may be contained in the black resin film of the invention in the case where it is produced by coating include the following solvents.

The solvent used may be a solvent that is ordinarily used without particular limitation. Specific examples thereof include an ester compound, an ether compound, a ketone compound and an aromatic hydrocarbon compound.

Examples thereof that may be preferably used in the invention include methyl ethyl ketone, propylene glycol monomethyl ether, propylene glycol monomethyl ether acetate, cyclohexanone, cyclohexanol, methyl isobutyl ketone, ethyl lactate and methyl lactate, as similar to the solvents described in the paragraphs [0054] to [0055] of US 2005/282073A1.

Among these solvents, methyl 3-ethoxypropionate, ethyl 3-ethoxypropionate, ethyl cellosolve acetate, ethyl lactate, butyl acetate, methyl 3-methoxypropionate, 2-heptanone, cyclohexanone, diethylene glycol monoethyl ether acetate (ethylcarbitol acetate), diethylene glycol monobutyl ether acetate (butylcarbitol acetate), propylene glycol methyl ether acetate, methyl ethyl ketone and the like are preferably used as the solvent in the invention. The solvents may be used solely or as a combination of two or more kinds thereof.

In the invention, an organic solvent having a boiling point of from 180 to 250° C. may be used depending on necessity. Examples of the high boiling point solvent include diethylene glycol monobutyl ether, diethylene glycol monoethyl ether acetate, diethylene glycol monoethyl ether, 3,5,5-trimethyl-2-cyclohexen-1-one, dipropylene glycol monomethyl ether acetate, propylene glycol diacetate, propylene glycol n-propyl ether acetate, diethylene glycol diethyl ether, 2-ethylhexyl acetate, 3-methoxy-3-methylbutyl acetate, γ-butyrolactone, tripropylene glycol methyl ether acetate, dipropylene glycol n-butyl acetate, propylene glycol phenyl ether acetate and 1,3-butanediol diacetate.

The black resin film of the invention preferably contains, as the solvent, a first solvent that has an evaporation rate of 200% or more of butyl acetate and a second solvent that has an evaporation rate of 50% or less of butyl acetate.

The black resin film of the invention preferably contains, as the solvent, a solvent that is a polyhydric alcohol derivative and a solvent that is a ketone.

Characteristics

Bulk Strength after heating

Figure 9:
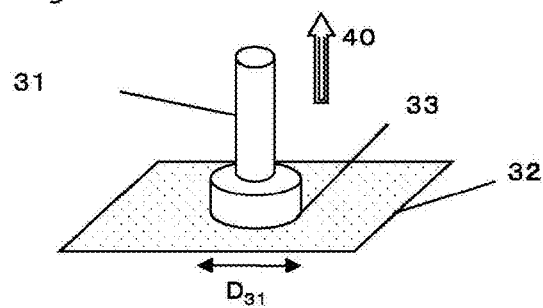
FIG. 9 is an illustrative view showing evaluation of a bulk strength of a black resin film (i.e., a decorative material).

The black resin film of the invention has a bulk strength after heating to 240° C. for 80 minutes and further heating to 300° C. for 30 minutes of 100 N per 1.6 mm in diameter or more. The bulk strength referred herein is a value that is measured by the Sebastian's method. The Sebastian's method is an experimental method, in which as shown in FIG. 9, a metallic pin adhered to the resin film is pulled vertically, and a force where the pin is peeled off is measured, by which the bulk strength of the film and the adhesion force may be measured. For example, equipments therefor are available as Romulus, produced by Quad Group, Inc., but the invention is not limited thereto.

In the description, as shown in FIG. 9, an aluminum pin 31 having a diameter of the bottom surface thereof of 1.6 mm is adhered to the surface of the black resin film 32 (i.e., the decorative material) with an epoxy adhesive, and after curing the epoxy adhesive, the aluminum pin 31 is pulled in a direction that is perpendicular to the black resin film 32 (i.e., the peeling direction 40 of the aluminum pin), thereby measuring the maximum load where the aluminum pin is peeled off. An epoxy adhesive-attached aluminum pin (adhesive-attached aluminum pin 2.7 mm, Model #901106, produced by Quad Group, Inc.) is used herein.

The black resin film of the invention preferably has a bulk strength after heating to 240° C. for 80 minutes and further heating to 300° C. for 30 minutes of 130 N per 1.6 mm in diameter or more, more preferably 140 N per 1.6 mm in diameter or more, particularly preferably 150 N per 1.6 mm in diameter or more, and further particularly preferably 170 N per 1.6 mm in diameter or more.

Thermal Weight Reduction Rate after Heating

The black resin film of the invention preferably has a thermal weight reduction rate after heating to 240° C. for 80 minutes and further heating to 300° C. for 30 minutes of 39.2% or less, and more preferably 36.0% or less. The control of the thermal weight reduction rate of the black resin film of the invention having the aforementioned preferred composition to the aforementioned range may facilitates that the bulk strength after heating thereof is in the preferred range.

The thermal weight reduction rate of the black resin film of the invention may be a value that is measured after heating to 240° C. for 80 minutes and further heating to 300° C. for 30 minutes by using TGA.

Shape

Thickness

The black resin film of the invention preferably has a thickness of from 1.5 to 5.0 μm from the standpoint of enhancing the bulk strength after heating while providing a suitable black density, and more preferably from 1.5 to 1.8 μm.

Taper Angle

The black resin film of the invention preferably has a taper angle on a side surface thereof that satisfies the following expression (1) and the following expression (2). The black resin film of the invention may have a part of the side surface thereof that forms a convex or concave curved surface, and preferably forms a convex curved surface, through a development and the like in the method for producing a black resin film of the invention described later.

$$\Theta_1 \leq 40°$$ Expression (1)

wherein $\Theta_1$ represents an angle that is 90° or less among angles formed between the straight line $l_{12}$ and the extended line $l_A$ of the bottom surface of the black resin film, in which the straight line $l_{12}$ passes through an intersecting point $C_1$ and an intersecting point $C_2$, the intersecting point $C_1$ is an intersecting point of the side surface of the black resin film and the straight line at a 1/4 height from the surface of the black resin film on the side of the substrate when the height of the black resin film is divided into four equal parts, and the intersecting point $C_2$ is an intersecting point of the side surface of the black resin film and the straight line at a 2/4 height from the surface of the black resin film on the side of the substrate when the height of the black resin film is divided into four equal parts.

$$\Theta_2 \leq 40°$$ Expression (2)

wherein $\Theta_2$ represents an angle that is 90° or less among angles formed between the straight line $l_{23}$ and the extended line $l_B$ of a portion of the top surface of the black resin film that is approximately in parallel to the bottom surface of the black resin film, in which the straight line $l_{23}$ passes through an intersecting point $C_2$ and an intersecting point $C_3$, the intersecting point $C_2$ is an intersecting point of the side surface of the black resin film and the straight line at a 2/4 height from the surface of the black resin film on the side of the substrate when the height of the black resin film is divided into four equal parts, and the intersecting point $C_3$ is an intersecting point of the side surface of the black resin film and the straight line at a 3/4 height from the surface of the black resin film on the side of the substrate when the height of the black resin film is divided into four equal parts.

Among the taper angles on the side surface of the black resin film of the invention, $\Theta_1$ and $\Theta_2$ each are preferably 40° or less, more preferably $\Theta_1$ or $\Theta_2$ is 35° or less, and particularly preferably $\Theta_1$ and $\Theta_2$ each are 35° or less.

Figure 10:
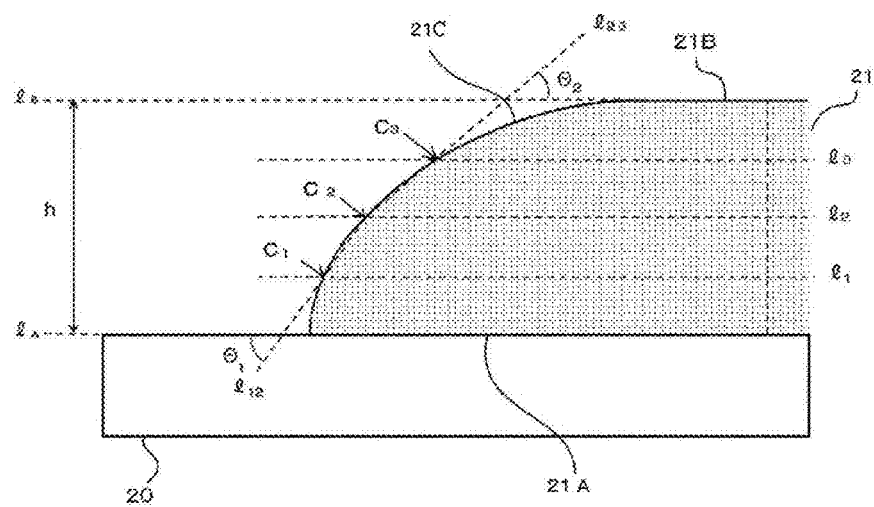
FIG. 10 is an illustrative view showing taper angles of a black resin film (i.e., a decorative material).

The taper angle on the side surface of the black resin film of the invention may be obtained according to FIG. 10 from a cross sectional photograph of the black resin film (decorative material) obtained by photographing the black resin film (decorative material) with SEM in the just lateral direction at an inclination angle of 0°. The details thereof will be described in the evaluation of the thickness and the taper angle of the black resin film (decorative material) in the examples described later.

Method for Producing Black Resin Film

The method for producing a black resin film of the invention (which may be hereinafter referred to as the production method of the invention) contains applying a photosensitive resin composition containing a black pigment, an alkali-soluble polymer compound, an ethylenic unsaturated bond-containing compound and a photopolymerization initiator, to a substrate, exposing the photosensitive resin composition on the substrate, developing the photosensitive resin composition thus exposed, and performing post-exposure after the development, and satisfies the following condition (A) or the following condition (B):

Condition (A): the photopolymerization initiator is an α-aminoalkylphenone compound or an α-hydroxyalkylphenone compound, and Condition (B): the post-exposure after the development is performed from both a surface of the photosensitive composition on a side that is in contact with the substrate and a surface thereof on a side that is not in contact with the transparent substrate.

By satisfying the condition (A) or the condition (B), the bulk strength after heating may be controlled to the range of the invention.

The method for producing a black resin film of the invention preferably satisfies both the condition (A) and the condition (B) from the standpoint of enhancing the bulk strength after heating.

Step of Applying Photosensitive Resin Composition to Substrate

First, a step of applying the photosensitive resin composition to the substrate will be described.

Substrate

In the method for producing a black resin film of the invention, the substrate is preferably a transparent substrate (i.e., a translucent substrate) from the standpoint that the post-exposure may be performed both the surfaces of the black resin film.

In the method for producing a black resin film of the invention, the transparent substrate is preferably an insulating transparent substrate from the standpoint that the black resin film of the invention is used as a front plate of a capacitance type input device.

The substrate is preferably constituted by a translucent substrate, and for example, toughened glass represented by Gorilla Glass, available from Corning Inc. may be used.

Photosensitive Film

The method of applying the photosensitive resin composition to the substrate is not particularly limited, and known methods may be used, examples of which include coating and transferring.

Among these, in the method for producing a black resin film of the invention, the photosensitive resin composition is preferably transferred from a photosensitive transfer film, which contains a provisional support having accumulated thereon the photosensitive resin composition, to the substrate.

In a method of forming a decorative material or a transparent electrode pattern by using a dry film resist having a provisional support having formed thereon only a photocurable resin layer, the black resin film (decorative material) formed on the back surface of the front plate is required to have light shielding property, but there are problems that light leakage may occur due to bubbles formed on dry film lamination, and in the case where the dry film is laminated over both the black resin film (decorative material), which requires a certain thickness (several micrometers for a black layer) from the standpoint of the light shielding property, and the back surface of the front plate, bubbles may remain at the step in thickness at the edge of the black resin film (decorative material) of the invention. In the more preferred embodiment of the method for producing a black resin layer (decorative material) of the invention, the taper angles of the black resin film (decorative material) may be reduced, and thereby formation of bubbles may be suppressed even when a photosensitive transfer film is used.

The photosensitive film used in the production method of the invention will be described.

Photocurable Resin Layer

The photosensitive film contains a photocurable resin layer, to which an additive is added depending on the purpose thereof. Specifically, in the case where the photosensitive film is used for forming a decorative material, a photosensitive resin composition containing the black pigment, the alkali-soluble polymer compound, the ethylenic unsaturated bond-containing compound and the photopolymerization initiator used in the method for producing a black resin film of the invention is used in the photocurable resin layer.

The photocurable resin layer of the photosensitive film may further contain a colorant, an additive and the like, but what is contained therein is not limited thereto.

The thickness of the photocurable resin layer containing the black pigment is preferably from 0.5 to 10 μm, more preferably from 0.8 to 5 μm, and particularly preferably from 1 to 3 μm, from the standpoint of the difference in thickness from the other layers. The content of the colorant in the colored photocurable resin layer is not particularly limited, and is preferably from 15 to 70% by mass, more preferably from 20 to 60% by mass, and further preferably from 25 to 50% by mass, from the standpoint of reducing the development time sufficiently.

The total solid content referred herein means the total mass of the non-volatile components in the colored photocurable resin layer except for the solvent and the like.

Provisional Support

The provisional support used may be a material that has flexibility and does not undergo significant deformation, contraction and elongation under pressure or under pressure and heat. Examples of the support include a polyethylene terephthalate film, a cellulose triacetate film, a polystyrene film and a polycarbonate film, and among these, a biaxially stretched polyethylene terephthalate film is particularly preferred.

The thickness of the provisional support is not particularly limited and is generally in a range of from 5 to 200 μm, and preferably in a range of from 10 to 150 μm particularly in view of the handleability and the versatility.

The provisional support may be transparent and may contain dye silicon, alumina sol, a chromium salt, a zirconium salt or the like.

The provisional support may have conductivity imparted by the method described in JP-A-2005-221726 and the like.

Thermoplastic Resin Layer

The photosensitive film preferably has a thermoplastic resin layer provided between the provisional support and the photocurable resin layer. As compared to the case where the black resin film (decorative material) and the like are formed by using a photosensitive film having no thermoplastic resin layer, the use of the photosensitive film having the thermoplastic resin layer may prevent bubbles from being formed in the black resin layer (decorative material) formed by transferring the photocurable resin layer, and thus the image display apparatus may be prevented from suffering image unevenness and the like, thereby providing excellent display characteristics.

The photosensitive film preferably has a thermoplastic resin layer provided between the provisional support and the photocurable resin layer. The thermoplastic resin layer is preferably alkali-soluble. The thermoplastic resin layer may exhibit a function as a cushioning material for absorbing the unevenness on the surface of the underlayer (including the unevenness due to the image and the like having been formed thereon), and preferably has such a property that the layer is capable of being deformed corresponding to the unevenness on the target surface.

The thermoplastic resin layer preferably has an embodiment containing the polymer substance described in JP-A-5-72724 as a component, and particularly preferably has an embodiment containing at least one selected from organic polymer substances having a softening point of approximately 80° C. or less measured by a Vicart method (which may be specifically the polymer softening point measurement method according to ASTM D1235).

Specific examples thereof include a polyolefin, such as polyethylene and polypropylene, an ethylene copolymer of ethylene and vinyl acetate or a saponified product thereof or the like, a copolymer of ethylene and an acrylate ester or a saponified product thereof, polyvinyl chloride or a vinyl chloride copolymer of vinyl chloride and vinyl acetate or a saponified product thereof or the like, polyvinylidene chloride, a vinylidene chloride copolymer, polystyrene, a styrene copolymer of styrene and a (meth)acrylate ester or a saponified product thereof or the like, polyvinyltoluene, a vinyltoluene copolymer of vinyltoluene and a (meth)acrylate ester or a saponified product thereof or the like, a poly(meth)acrylate ester, a (meth)acrylate ester copolymer of butyl (meth)acrylate and vinyl acetate or the like, and a polyamide resin, such as a vinyl acetate copolymer nylon, a copolymer nylon, an N-alkoxymethylated nylon and an N-dimethylaminated nylon.

The thickness of the thermoplastic resin layer is preferably from 3 to 30 μm. When the thickness of the thermoplastic resin layer is less than 3 μm, the layer may have insufficient followability on lamination and thus may not absorb the unevenness on the surface of the underlayer completely. When the thickness of the layer exceeds 30 μm, the load on drying (removing the solvent) for forming the thermoplastic resin layer on the provisional support may be increased, the period of time for developing the thermoplastic resin layer may be increased, and the processability may be deteriorated. The thickness of the thermoplastic resin layer is more preferably from 4 to 25 μm, and particularly preferably from 5 to 20 μm.

The thermoplastic resin layer may be formed by coating or the like a preparation liquid containing the thermoplastic organic polymer, and the preparation liquid used on coating or the like may be prepared by using a solvent. The solvent is not particularly limited as far as it dissolves the polymer component constituting the layer, and examples thereof include methyl ethyl ketone, cyclohexanone, propylene glycol monomethyl ether acetate, n-propanol and 2-propanol.

Viscosity of Thermoplastic Resin Layer and Photocurable Resin Layer

The thermoplastic resin layer preferably has a viscosity measured at 100° C. in a range of from 1,000 to 10,000 Pa·sec, and the photocurable resin layer preferably has a viscosity measured at 100° C. in a range of from 2,000 to 50,000 Pa·sec, which preferably satisfy the following expression (A):

(viscosity of thermoplastic resin layer)<(viscosity of photocurable resin layer)   Expression (A)

The viscosities of the layers may be measured in the following manner. The solvent is removed from the thermoplastic resin layer or the photocurable resin layer by drying under atmospheric pressure and drying under reduced pressure to prepare a measurement specimen, which is measured under condition of a measurement start temperature of 50° C., a measurement end temperature of 150° C., a temperature raising rate of 5° C. per minute and a frequency of 1 Hz/deg, for example, with Rheovibron (model DD-III, produced by Baldwin Japan, Ltd.), and the measurement value at 100° C. is used.

Additional Layer

The photosensitive film may be properly constituted by providing an intermediate layer between the photocurable resin layer and the thermoplastic resin layer, and a protective film on the surface of the photocurable resin layer.

The photosensitive film preferably has an intermediate layer for the purpose of preventing the components from being mixed on coating plural layers and on storage after coating plural layers. The intermediate layer is preferably an oxygen shielding film having an oxygen shielding function, which is described as the separating layer in JP-A-5-72724, and thus the sensitivity on exposure is enhanced to reduce the time load of the exposure machine, thereby enhancing the productivity.

Examples of the intermediate layer and the protective film include ones described in the paragraphs [0083] to [0087] and [0093] of JP-A-2006-259138, which may be appropriately used.

Method for producing Photosensitive Film

The photosensitive film may be produced according to the production method of a photosensitive transfer material described in the paragraphs [0094] to [0098] of JP-A-2006-259138.

Specifically, in the case where the photosensitive film having an intermediate layer is produced, the photosensitive film may be favorably produced in such a manner that a solution containing a thermoplastic organic polymer and an additive dissolved therein (i.e., a coating liquid for a thermoplastic resin layer) is coated and dried on a provisional support to form a thermoplastic resin layer, then a preparation liquid, which is prepared by adding a resin and an additive to a solvent that does not dissolve the thermoplastic resin layer, (i.e., a coating liquid for an intermediate layer) is coated and dried on the thermoplastic resin layer to form an intermediate layer, and a coating liquid for a colored photosensitive resin layer, which is prepared by using a solvent that does not dissolve the intermediate layer, is further coated and dried on the intermediate layer to laminate a colored photosensitive layer.

Method for Applying Decorative Material on Substrate by Using Photosensitive Film In the case where the black resin film (decorative material) of the invention is applied to the substrate by using the photosensitive film, a patterning method using the photosensitive film will be described.

Examples of the method of applying the decorative material to the substrate includes a method containing a cover film removing step of removing the cover film from the photosensitive film, and a transferring step of transferring the photosensitive resin layer of the photosensitive transfer material, from which the cover film has been removed, to the substrate.

Transferring Step

The transferring step is a step of transferring the photocurable resin layer of the photosensitive film, from which the cover film has been removed, to the substrate.

In this case, such a method is preferred that the photocurable resin layer of the photosensitive film is laminated to the substrate, and then the provisional support is removed.

The photocurable resin layer may be transferred (adhered) to the surface of the substrate by superimposing the photocurable resin layer to the surface of the substrate, to which pressure and heat are applied. The adhesion may be performed with a known laminator, such as a laminator, a vacuum laminator, and an automatic cutting laminator capable of enhancing the productivity.

Step of Exposing Photosensitive Resin Composition on Substrate

The method for producing a black resin film of the invention contains a step of exposing the photosensitive resin composition on the substrate.

In the case where the black resin film (decorative material) of the invention is applied to the substrate by using the photosensitive film, the exposing step is preferably a step of exposing the photocurable resin layer having been transferred to the substrate.

Specific examples of the method include a method of disposing a prescribed mask on the photocurable resin layer formed on the substrate, and then exposing the photocurable resin layer from above the mask through the mask, the thermoplastic resin layer and the intermediate layer.

For the light source for exposure, ones capable of radiating light having a wavelength range capable of curing the photocurable resin layer (for example, 360 nm, 405 nm or the like) may be appropriately selected and used. Specific examples thereof include a super-high pressure mercury lamp, a high pressure mercury lamp and a metal halide lamp. The exposure amount is generally approximately from 5 to 200 $mJ/cm^2$, and preferably approximately from 10 to 100 $mJ/cm^2$.

Developing Step

The method for producing a black resin film of the invention contains a step of developing the photosensitive resin composition having been exposed.

The development may be performed by using a developer liquid. The developer liquid is not particularly limited, and known developer liquids described, for example, in JP-A-5-72724 may be used. The developer liquid preferably induces a dissolution type development behavior of the photocurable resin layer, and preferably contains a compound having pKa of from 7 to 13 in a concentration of from 0.05 to 5 mol/L, but a small amount of an organic solvent that is miscible with water may be added thereto. Examples of the organic solvent that is miscible with water include methanol, ethanol, 2-propanol, 1-propanol, butanol, diacetone alcohol, ethylene glycol monomethyl ether, ethylene glycol monoethyl ether, ethylene glycol mono-n-butyl ether, benzyl alcohol, acetone, methyl ethyl ketone, cyclohexanone, ε-caprolactone, γ-butyrolactone, dimethylformamide, dimethylacetamide, hexamethylphosphoramide, ethyl lactate, methyl lactate, ε-caprolactam and N-methylpyrrolidone. The concentration of the organic solvent is preferably from 0.1 to 30% by mass.

The developer liquid may contain a known surfactant. The concentration of the surfactant is preferably from 0.01 to 10% by mass.

The developing method may be any of paddle developing, shower developing, shower and spin developing, and dip developing. The shower developing will be described. The developer liquid may be sprayed by showering onto the photocurable resin layer after exposing, thereby removing the uncured portion. In the case where the thermoplastic resin layer and the intermediate layer are provided, the thermoplastic resin layer, the intermediate layer and the like are preferably removed before developing, in such a manner that an alkaline liquid that has low solubility to the photocurable resin layer is sprayed by showering thereto. After developing, the development residue is preferably removed by spraying a rinsing liquid by showering while rubbing with a brush or the like. The developer liquid preferably has a temperature of from 20 to 40° C. and pH of from 8 to 13.

Post-Exposing Step

The method for producing a black resin film of the invention contains a step of performing post-exposure after the developing step.

The method for producing a black resin film of the invention satisfies the condition (A) or the condition (B), and in the case where the condition (A), i.e., the photopolymerization initiator is an α-aminoalkylphenone compound or an α-hydroxyalkylphenone compound, is satisfied, the post-exposing step may be performed only from the surface of the photosensitive composition on the side that is in contact with the substrate, only from the surface thereof on the side that is not in contact with the transparent substrate, from both the surfaces thereof.

In the case where the condition (A) or the condition (B), and in the case where the condition (A), i.e., the photopolymerization initiator is an α-aminoalkylphenone compound or an α-hydroxyalkylphenone compound, is not satisfied, the post-exposing step necessarily satisfies the condition (B), i.e., the post-exposure after the developing step is performed from both the surface of the photosensitive composition on the side that is in contact with the substrate and the surface thereof on the side that is not in contact with the transparent substrate.

In the method for producing a black resin film of the invention, the post-exposing step is performed while satisfying the conditions, and thereby the bulk strength after heating of the black resin film may be enhanced.

In the method for producing a black resin film of the invention, the exposure amount in the post-exposure after the developing step is preferably 1,300 mJ/cm$^2$ or more, and more preferably 2,000 mJ/cm$^2$ or more, in terms of i line.

Additional Steps

The method for producing a black resin film of the invention may have additional steps, such as a post-baking step.

For the exposing step, the developing step and the additional steps, the methods described in the paragraphs [0035] to [0051] of JP-A-2006-23696 may also be preferably applied to the invention.

The patterning exposure may be performed after releasing the provisional support, or may be performed before releasing the provisional support, and then the provisional support is released. The exposure may be performed by using a mask or may be digital exposure using laser or the like.

Method for Producing Capacitance Type Input Device

The method for producing a capacitance type input device of the invention (which may be hereinafter referred to as the production method of the invention) is a production method of a capacitance type input device containing a front plate and on a non-contact surface thereof the following components (1) to (4), in which the component (1) is produced by the method for producing a black resin film of the invention:

(1) a decorative material, (2) plural first transparent electrode patterns that contain plural pad portions that are formed to extend in a first direction and connected through connecting portions, (3) plural second electrode patterns that are electrically insulated from the first transparent electrode patterns, and contain plural pad portions that are formed to extend in a direction intersecting the first direction, and (4) an insulating layer that electrically insulates the first transparent electrode patterns and the second electrode patterns from each other.

The capacitance type input device of the invention may further contain the following component (5):

(5) a conductive element that is other than the first transparent electrode patterns and the second electrode patterns and is electrically connected to at least one of the first transparent electrode patterns and the second electrode patterns.

In the capacitance type input device of the invention, the second electrode patterns may be transparent electrode patterns. While the second transparent electrode patterns may be described herein instead of the second electrode patterns, embodiments of the second electrode patterns may be the same as preferred embodiments of the second transparent electrode patterns.

Structure of Capacitance Type Input Device

The structure of the capacitance type input device produced by the production method of the invention will be described. FIG. 1 is across sectional view showing a structure of the capacitance type input device of the invention. In FIG. 1, a capacitance type input device 10 is constituted by a front plate 1, a decorative layer 2, first transparent electrode patterns 3, second transparent electrode patterns 4, an insulating layer 5, a conductive element 6 and a transparent protective layer 7.

The front plate 1 used may be the substrate in the method for producing a black resin film of the invention. In FIG. 1, the surface of the front plate 1 where the components are provided is referred to as a non-contact surface. In the capacitance type input device 10 of the invention, input may be performed by touching the contact surface of the front plate 1 (which is the opposite surface to the non-contact surface) with a finger or the like. The front plate may be hereinafter referred to as a substrate in some cases.

The decorative material 2 is provided on the non-contact surface of the front plate 1. The decorative material 2 is in a flame pattern surrounding the display region formed on the non-contact surface of the front plate of the touch-sensitive panel, and is formed to hide laid circuits and the like.

Figure 2:
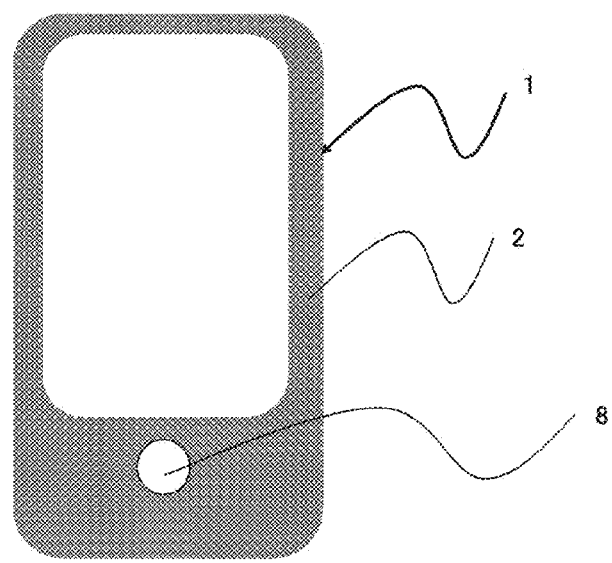
FIG. 2 is an illustrative view showing an example of a front plate in the invention.

In the capacitance type input device 10 of the invention, as shown in FIG. 2, the decorative material 2 is formed to cover a partial region of the front plate 1 (which is the region other than the input surface in FIG. 2). Furthermore, the front plate 1 may have an opening 8 in a part of the front plate as shown in FIG. 2. A mechanical push switch may be provided in the opening 8.

The front plate 1 has, formed on the non-contact surface thereof, plural first transparent electrode patterns 3 that contain plural pad portions that are formed to extend in a first direction and connected through connecting portions, plural second transparent electrode patterns 4 that are insulated from the first transparent electrode patterns 3 and contain plural pad portions that are formed to extend in a direction intersecting the first direction, and an insulating layer 5 that electrically insulates the first transparent electrode patterns 3 and the second electrode patterns 4 from each other. The first transparent electrode patterns 3, the second transparent electrode patterns 4 and a conductive element 6 described later may be produced with a transparent conductive metal oxide film, such as ITO (indium tin oxide) and IZO (indium zinc oxide). Examples of the metal film include an ITO film; a metal film, such as Al, Zn, Cu, Fe, Ni, Cr and Mo; and a metal oxide film, such as $SiO_2$. In this case, the thickness of the components may be from 10 to 200 nm. An amorphous ITO film may be converted to a polycrystalline ITO film by baking, thereby reducing the electric resistance. The first transparent electrode patterns 3, the second transparent electrode patterns 4 and a conductive element 6 described later may also be produced with a photosensitive film having a photocurable resin layer containing conductive fibers described later. In the case where the first transparent electrode patterns and the like are formed with ITO or the like, reference may be made to the paragraphs [0014] to [0016] of Japanese Patent No. 4,506785. [0073]

At least one of the first transparent electrode patterns 3 and the second transparent electrode patterns 4 may be provided over both regions in the non-contact surface of the front plate 1 and the surface of the decorative material 2 that is opposite to the front plate 1. FIG. 1 shows an illustration, in which the second transparent electrode patterns are provided over both regions in the non-contact surface of the front plate 1 and the surface of the decorative material 2 that is opposite to the front plate 1. In the case where the photosensitive film is laminated over the decorative material, which necessarily has a certain thickness, and the back surface of the front plate, as in this case, the photosensitive film of the invention having the particular layer structure may be laminated without occurrence of bubbles at the boundary of the mask by a simple process step without the use of an expensive equipment, such as a vacuum laminator.

Figure 3:
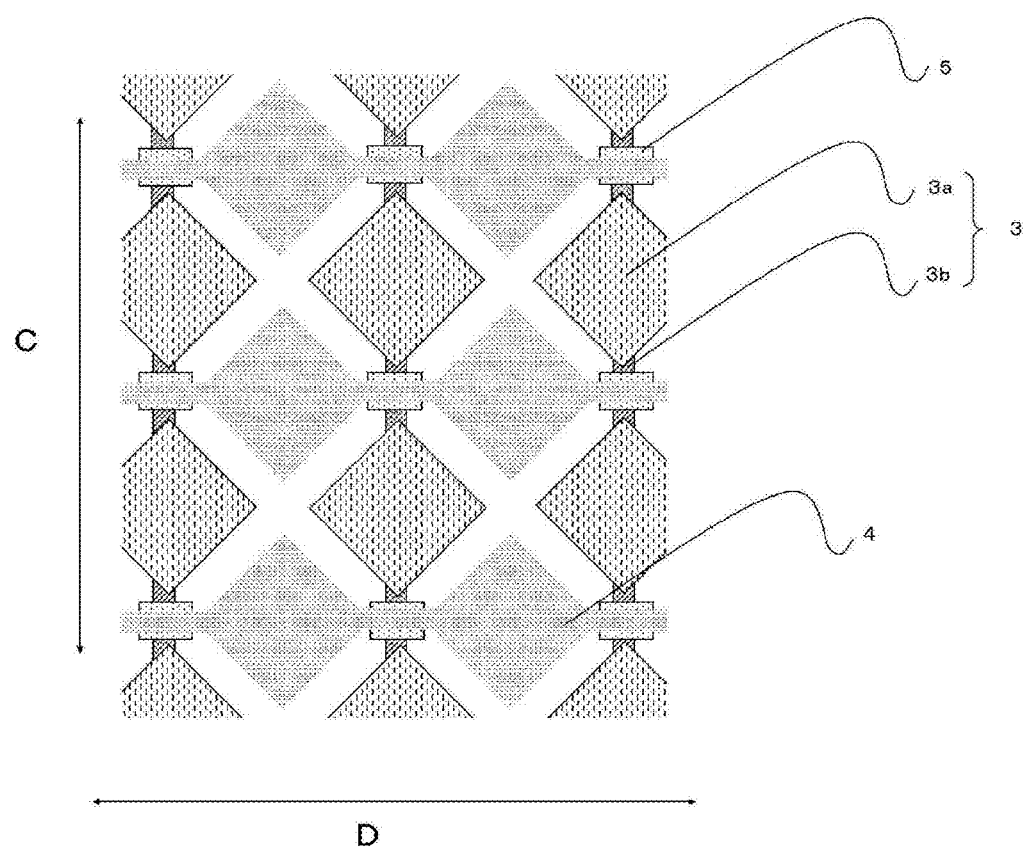
FIG. 3 is an illustrative view showing an example of first transparent electrode patterns and second transparent electrode patterns in the invention.

The first transparent electrode patterns 3 and the second transparent electrode patterns 4 will be described with reference to FIG. 3. FIG. 3 is an illustrative view showing an example of the first transparent electrode patterns and the second transparent electrode patterns in the invention. As shown in FIG. 3, the first transparent electrode patterns 3 contain pad portions 3a that are formed to extend in a first direction and connected through connecting portions 3b. The second transparent electrode patterns 4 are electrically insulated from the first transparent electrode patterns 3 with an insulating layer 5, and contain plural pad portions that are formed to extend in a direction intersecting the first direction (i.e., a second direction in FIG. 3). In the formation of the first transparent electrode patterns 3, the pad portions 3a and the connecting portions 3b may be produced integrally with each other, or may be produced in such a manner that only the connecting portions 3b are produced, and then the pad portions 3a and the second transparent electrode patterns 4 are produced (patterned) integrally with each other. In the case where the pad portions 3a and the second transparent electrode patterns 4 are produced (patterned) integrally with each other, the layers are formed to make such a structure as shown in FIG. 3 that a part of the connecting portions 3b and a part of the pad portions 3a are connected to each other, and the first transparent electrode patterns 3 and the second transparent electrode patterns 4 are electrically insulated from each other with the insulating layer 5.

In FIG. 1, a conductive element 6 is provided on the surface of the decorative material 2 that is opposite to the front plate 1. The conductive element 6 is electrically connected to at least one of the first transparent electrode patterns 3 and the second electrode patterns 4, and is an element that is other than the first transparent electrode patterns 3 and the second electrode patterns 4. FIG. 1 shows an illustration, in which the conductive element 6 is connected to the second transparent electrode patterns 4.

As shown in FIG. 1, a transparent protective layer 7 is provided to cover the entire of the constitutional components. The transparent protective layer 7 may be constituted to cover apart of the constitutional components. The insulating layer 5 and the transparent protective layer 7 may be formed of the same material or different materials. The material constituting the insulating layer 5 and the transparent protective layer 7 preferably has a high surface hardness and a high heat resistance, and examples thereof used include a known photosensitive siloxane resin material and a known acrylic resin material.

In the method for producing a capacitance type input device of the invention, at least one of the components (1) to (5) is preferably formed by using a photosensitive film having a provisional support, a thermoplastic resin layer and a photocurable resin layer in this order.

In the production method of the invention, at least one component of the decorative material 2, the first transparent electrode patterns 3, the second transparent electrode patterns 4, the insulating layer 5, the conductive element 6, and depending on necessity the transparent protective layer 7 is preferably formed by using a photosensitive film having a provisional support having accumulated thereon the photosensitive resin composition, and is more preferably formed by using a photosensitive film having a provisional support having thereon a thermoplastic resin layer and a photocurable resin layer in this order.

The decorative material 2, the insulating layer 5 and the transparent protective layer 7 are preferably formed by transferring the photocurable resin layer by using the photosensitive film to the front plate 1. For example, in the case where the decorative material 2 is formed, the photosensitive film that has a black photocurable resin layer as the photocurable resin layer is used, and the black photocurable resin layer is transferred to the surface of the front plate 1 to form the decorative layer 2. In the case where the insulating layer 5 is formed, the photosensitive film that has an insulating photocurable resin layer as the photocurable resin layer is used, and the photocurable resin layer is transferred to the surface of the front plate 1 having the first transparent electrode patterns having been formed thereon to form the insulating layer 5. In the case where the transparent protective layer 7 is formed, the photosensitive film that has a transparent photocurable resin layer as the photocurable resin layer is used, and the photocurable resin layer is transferred to the surface of the front plate 1 having the components having been formed thereon to form the transparent protective layer 7.

In the case where the decorative material 2 and the like are formed by using the photosensitive film, even though the substrate (front plate) has an opening, leakage of a resist component from the opening may be prevented from occurring, and protrusion of a resist component may be prevented from occurring from the edge of the glass at the decorative material, which necessarily forms a light-shielding pattern up to the edge of the front plate. Accordingly, the back surface of the substrate may be prevented from being contaminated, and a touch-sensitive panel that is advantageously reduced in thickness and weight may be produced by a convenient process.

Furthermore, the use of the photosensitive film having the particular layer structure that has the thermoplastic resin layer between the photocurable resin layer and the provisional support for forming the decorative material 2 required to have light shielding property may prevent formation of bubbles on laminating the photosensitive film, thereby forming the decorative material 2 and the like having high quality without leakage of light.

The first transparent electrode patterns 3, the second transparent electrode patterns 4 and the conductive element 6 may be formed by an etching treatment or by using a photosensitive film having a conductive photocurable resin layer.

In the case where the first transparent electrode patterns 3, the second transparent electrode patterns 4 and the conductive element 6 are formed by an etching treatment, a transparent electrode layer, such as ITO, is formed by sputtering on the non-contact surface of the front plate 1 having the decorative material 2 and the like formed thereon. Subsequently, an etching pattern is formed on the transparent electrode layer through exposure and development of the photosensitive film having a photocurable resin layer for etching as the photocurable resin layer. Thereafter, the transparent electrode layer is etched to pattern the transparent electrode, and then the etching pattern is removed, thereby forming the first transparent electrode patterns 3 and the like.

In the case where the first transparent electrode patterns 3, the second transparent electrode patterns 4 and the conductive element 6 are formed by using the photosensitive film having the conductive photocurable resin layer, they may be formed by transferring the conductive photocurable resin layer to the surface of the front plat 1.

By forming the first transparent electrode patterns 3 by using the photosensitive film having the conductive photocurable resin layer, leakage of a resist component from an opening even using the substrate (front plate) having the opening may be prevented from occurring, whereby the back surface of the substrate may be prevented from being contaminated, and a touch-sensitive panel that is advantageously reduced in thickness and weight may be produced by a convenient process.

Furthermore, the use of the photosensitive film of the invention having the particular layer structure that has the thermoplastic resin layer between the conductive photocurable resin layer and the provisional support for forming the first transparent electrode patterns 3 and the like may prevent formation of bubbles on laminating the photosensitive film, thereby forming the first transparent electrode patterns 3, the second transparent electrode patterns 4 and the conductive element 6 that are excellent in conductivity with a low resistance.

Figure 4:
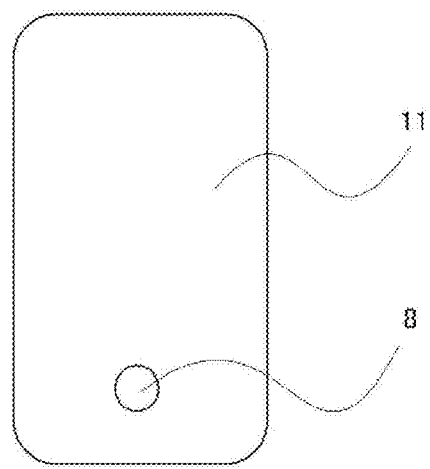
FIG. 4 is a top view showing an example of toughened glass having an opening therein.
Figure 5:
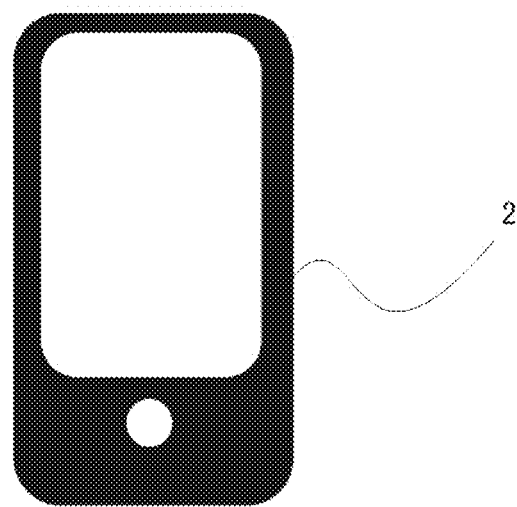
FIG. 5 is a top view showing an example of a front plate having a black resin film (i.e., a decorative material) of the invention.
Figure 6:
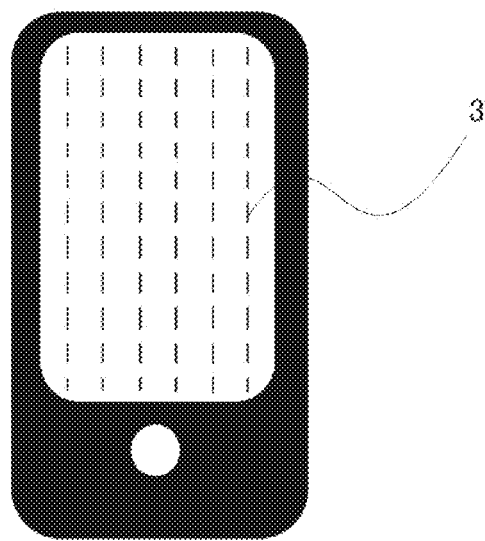
FIG. 6 is a top view showing an example of a front plate having first transparent electrode patterns formed thereon.
Figure 7:
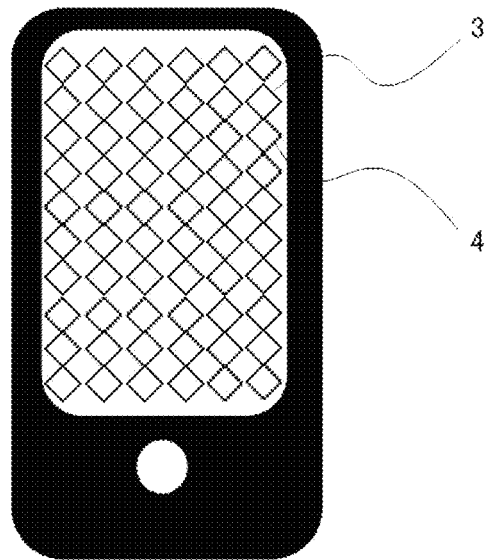
FIG. 7 is a top view showing an example of a front plate having first and second transparent electrode patterns formed thereon.
Figure 8:
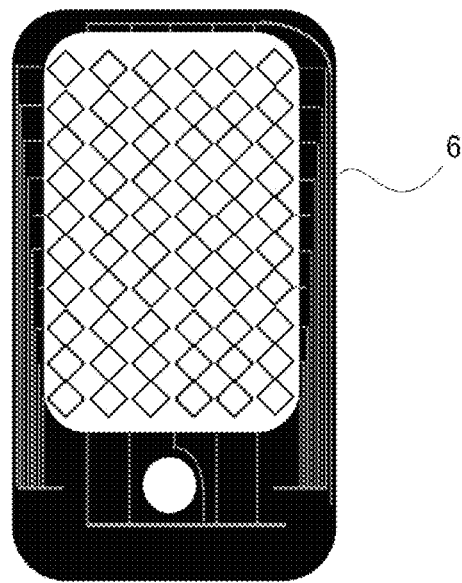
FIG. 8 is a top view showing an example of a front plate having a conductive element that is other than first and second transparent electrode patterns.

Examples of the embodiments formed in the course of the production method of the invention include the embodiments shown in FIGS. 4 to 8. FIG. 4 is a top view showing an example of toughened glass 11 having an opening 8 therein. FIG. 5 is a top view showing an example of a front plate having a decorative material 2 formed thereon. FIG. 6 is a top view showing an example of a front plate having first transparent electrode patterns 3 formed thereon. FIG. 7 is a top view showing an example of a front plate having first transparent electrode patterns 3 and second transparent electrode patterns 4 formed thereon. FIG. 8 is a top view showing an example of a front plate having a conductive element 6 that is other than first transparent electrode patterns and second electrode patterns.

These are examples embodying the aforementioned description, and the scope of the invention is not construed as being limited by the drawings.

Conductive Photocurable Resin Layer (Conductive Fibers)

In the case where the photosensitive film having the conductive photocurable resin layer laminated thereon is used for forming the transparent electrode patterns or the conductive element, conductive fibers shown below or the like may be used in the photocurable resin layer.

The structure of the conductive fibers is not particularly limited and may be appropriately selected depending on the purpose, and any one of a solid structure and a hollow structure is preferred.

Fibers having a solid structure may be referred to as "wires", and fibers having a hollow structure may be referred to as "tubes". Conductive fibers having an average short axis length of from 5 to 1,000 nm and an average long axis length of from 1 to 100 μm may be referred to as "nanowires".

Conductive fibers having a hollow structure having an average short axis length of from 1 to 1,000 nm and an average long axis length of from 0.1 to 1,000 μm may be referred to as "nanotubes".

The material of the conductive fibers is not particularly limited as far as it has conductivity, and may be appropriately selected depending on the purpose. At least one of a metal and carbon is preferred, and among these, the conductive fibers are preferably at least one of metal nanowires, metal nanotubes and carbon nanotubes.

Metal Nanowires

Metal

The material of the metal nanowires is not particularly limited and is preferably at least one kind of a metal selected from the group consisting of the fourth period, the fifth period and the sixth period of the long periodic table (IUPAC 1991), more preferably at least one kind of a metal selected from the groups 2 to 14, and further preferably at least one kind of a metal selected from the group 2, the group 8, the group 9, the group 10, the group 11, the group 12, the group 13 and the group 14, which is particularly preferably contained as a major component.

Examples of the metal include copper, silver, gold, platinum, palladium, nickel, tin, cobalt, rhodium, iridium, iron, ruthenium, osmium, manganese, molybdenum, tungsten, niobium, tantalum, titanium, bismuth, antimony, lead, and alloys thereof. Among these, ones containing silver as a major component and ones containing an alloy of silver and a metal other than silver are preferred.

The term "containing silver as a major component" means that the metal nanowires contain silver in an amount of 50% by mass or more, and preferably 90% by mass or more.

Examples of the metal used in the alloy with silver include platinum, osmium, palladium and iridium. These metals may be used solely or as a combination of two or more kinds thereof.

Shape

The shape of the metal nanowires is not particularly limited and may be appropriately selected depending on the purpose, and an arbitrary shape, such as a circular column shape, a rectangular parallelepiped shape and a column shape having a polygonal cross sectional shape, may be used. In a purpose that requires high transparency, a circular column shape and a shape having a polygonal cross sectional shape with rounded apexes are preferred.

The cross sectional shape of the metal nanowires may be examined in such a manner that a metal nanowire aqueous dispersion liquid is coated on a substrate, and the cross section thereof is observed with a transmission electron microscope (TEM).

The thickness of the conductive photocurable resin layer is preferably from 0.1 to 20 μm, more preferably from 0.5 to 18 μm, and particularly preferably from 1 to 15 μm, from the standpoint of the stability of the coating liquid and the processability including the drying after coating and the developing time on patterning. The content of the conductive fibers with respect to the total solid content of the conductive photocurable resin layer is preferably from 0.01 to 50% by mass, more preferably from 0.05 to 30% by mass, and particularly preferably from 0.1 to 20% by mass, from the standpoint of the conductivity and the stability of the coating liquid.

In the case where the insulating layer is formed by using the photosensitive film, the thickness of the photocurable resin layer is preferably from 0.1 to 5 μm, more preferably from 0.3 to 3 μm, and particularly preferably from 0.5 to 2 μm, from the standpoint of the maintenance of the insulating property.

In the case where the transparent protective layer is formed by using the photosensitive film, the thickness of the photocurable resin layer is preferably from 0.5 to 10 μm, more preferably from 0.8 to 5 μm, and particularly preferably from 1 to 3 μm, from the standpoint of sufficient exertion of the surface protective function.

Method for Producing Capacitance Type Input Device

In the method for producing a capacitance type input device of the invention, at least one component of the decorative material, the first transparent electrode patterns, the second transparent electrode patterns, the insulating layer, the conductive elements and depending on necessity the transparent protective layer is preferably formed by using the photosensitive film having the provisional support having thereon the thermoplastic resin layer and the photocurable resin layer in this order.

In the case where a permanent material, such as the decorative material, the insulating layer, the transparent protective layer, and the first transparent electrode patterns, the second transparent electrode patterns and the conductive element, which are formed with the conductive photocurable resin layer, is formed by using the photosensitive film, the photosensitive film is laminated on the substrate, exposed in the form of the target pattern, and then developed for removing the non-exposed regions in the case of the negative type material or the exposed regions in the case of the positive type material, thereby providing the pattern. In the development in this case, the thermoplastic resin layer and the photocurable layer may be removed by development with different liquids or may be removed with the different liquid. A known developing equipment, such as a brush or a high-pressure jet, may be used in combination depending on necessity. After the development, post exposure and post baking may be performed.

For enhancing the adhesiveness of the photosensitive resin layer by lamination in the later transferring step, the non-contact surface of the substrate (front plate) may be subjected to a surface treatment in advance. The surface treatment performed is preferably a surface treatment using a silane compound (i.e., a silane coupling treatment). The silane coupling agent used preferably has a functional group that undergoes mutual action with the photosensitive resin. For example, a silane coupling solution (a 0.3% by mass aqueous solution of N-β-(aminoethyl)-γ-aminopropyltrimethoxysilane, KBM603, a trade name, produced by Shin-Etsu Chemical Co., Ltd.) is sprayed to the surface by showering for 20 seconds, and then the surface is rinsed with pure water. Thereafter, the silane coupling agent is reacted by heating. A heating chamber may be used, and the reaction may be accelerated by preliminary heating for the substrate with a laminator.

The first transparent electrode patterns, the second transparent electrode patterns and other conductive members may also be formed by using the photosensitive film as a lift-off material. In this case, after patterning by using the photosensitive film, a transparent conductive layer is formed on the entire surface of the substrate, and then the photocurable resin layer of the invention is removed along with the transparent conductive layer accumulated thereon, thereby providing the target transparent electrode patterns (i.e., a lift-off method).

Case Using Photosensitive Film Used as Etching Resist

In the case where the photosensitive film of the invention is used as an etching resist (i.e., the etching pattern), the resist pattern may be obtained in the similar manner as above. In the etching treatment, etching and removal of the resist may be performed by a known method described in the paragraphs [0048] to [0054] of JP-A-2010-152155 and the like.

Examples of the etching method include a wet etching method by immersing in an etching liquid, which is ordinarily performed. The etching liquid used in the wet etching method may be selected from an acidic type and an alkaline type depending on the target of etching. Examples of the acidic type etching liquid include an aqueous solution containing a sole acidic component, such as hydrochloric acid, sulfuric acid, hydrofluoric acid or phosphoric acid, and a mixed aqueous solution of the acidic component and a salt, such as ferric chloride, ammonium fluoride or potassium permanganate. The acidic component may be a mixture of plural acidic components. Examples of the alkaline type etching liquid include an aqueous solution containing a sole alkaline component, such as sodium hydroxide, potassium hydroxide, ammonia, an organic amine or tetramethylammonium hydroxide, and a mixed aqueous solution of the alkaline component and a salt, such as potassium permanganate. The alkaline component may be a mixture of plural alkaline components.

The temperature of the etching liquid is not particularly limited and is preferably 45° C. or less. The resin pattern used as an etching mask (etching pattern) in the invention is formed by using the photocurable resin layer described above, and thereby exhibits excellent resistance to the acidic or alkaline etching liquid in the temperature range. Accordingly, the resin pattern is prevented from being released during the etching process, and thereby the portion having no resin pattern thereon is selectively etched.

After etching, a rinsing step and a drying step may be performed depending on necessity for preventing line contamination from occurring. For example, the rinsing step may be performed by rinsing the substrate with pure water at ordinary temperature for from 10 to 300 seconds, and the drying step may be performed by blowing air thereto at an air blowing pressure that is appropriately controlled (approximately from 0.1 to 5 $kg/cm^2$).

The subsequent method of releasing the resin pattern is not particularly limited, and examples thereof include a method of dipping the substrate in a releasing liquid at from 30 to 80° C., and preferably from 50 to 80° C., under stirring for from 5 to 30 minutes. The resin pattern used as the etching mask in the invention exhibits excellent chemical resistance at 45° C. or less as described above, but exhibits swelling property with an alkaline releasing liquid at a temperature of 50° C. or more. According to the property, the releasing step performed with a releasing liquid at from 50 to 80° C. provides such advantages that the period of time for the releasing step may be shortened, and the residue of the resin pattern after releasing may be reduced. Accordingly, by providing a difference in temperature between the liquids in the etching step and the releasing step, the resin pattern used as the etching mask in the invention exhibits good chemical resistance in the etching step, whereas exhibits good releasing property in the releasing step, and thus the resin pattern satisfies both the chemical resistance and the releasing property, which are contradictory to each other.

Examples of the releasing liquid include solutions obtained by dissolving an inorganic alkaline component, such as sodium hydroxide and potassium hydroxide, or an organic alkaline component, such as a tertiary amine and a quaternary ammonium salt, in water, dimethylsulfoxide, N-methylpyrrolidone, or a mixed solvent thereof. The releasing step may also be performed by a spraying method, a shower method, a paddle method or the like by using the releasing liquid.

Capacitance Type Input Device and Image Display Apparatus Containing Capacitance Type Input Device as Constitutional Component For the capacitance type input device that is produced by the production method of the invention and the image display apparatus containing the capacitance type input device as a constitutional component, the constitutions described, for example, in "Saishin Touch Panel Gijutsu" (Newest Touch-sensitive Panel Technology), published by Techno Times Co., Ltd., Jul. 6, 2009, "Touch Panel no Gijutsu to Kaihatsu" (Technology and Development of Touch-sensitive Panels), supervised by Yuji Mitani, CMC Publishing Co., Ltd., December 2004, Textbook for lecture in FPD International 2009 Forum T-11, Cypress Semiconductor Corporation, Application Note AN2292, and the like.

EXAMPLE

The invention will be described more specifically with reference to examples below.

The materials, the amounts used, the ratios, the contents of processes, the procedures of processes, and the like in the examples shown below may be appropriately changed unless they deviate from the substance of the invention. Accordingly, the scope of the invention is not construed as being limited to the specific examples shown below. The "%" and the "part" are based on mass unless otherwise indicated.

Example 1

Preparation of Black Resin Film (Decorative Material) of Invention
Preparation of Photosensitive Film 1 for forming Decorative Material On a polyethylene terephthalate film having a thickness of 75 μm as a provisional support, a coating liquid for a thermoplastic resin layer having the following formulation H1 was coated with a slit nozzle and dried. A coating liquid for an intermediate layer having the following formulation P1 was then coated and dried. A coating liquid for a black resist for a decorative material having the following formulation K1 was then further coated and dried. Thus, a thermoplastic resin layer having a dry thickness of 15.1 μm, an intermediate layer having a dry thickness of 1.6 μm and a black resist for a decorative material having a dry thickness of 2.0 μm to make an optical density of 3.35 were provided on the provisional support, and finally a protective film (a polypropylene film having a thickness of 12 μm) was adhered under pressure thereon. A transfer material having the provisional support, the thermoplastic resin layer, the intermediate layer (an oxygen shielding film) and the black resist for a decorative material integrated to each other was thus produced and designated as a specimen name, a photosensitive film 1 for forming a decorative material (a photosensitive film of Example 1).

| Coating Liquid for Thermoplastic Resin Layer, Formulation H1 | |
|---|---|
| Methanol | 11.1 parts by mass |
| Propylene glycol monomethyl ether acetate | 6.36 parts by mass |
| Methyl ethyl ketone | 52.4 parts by mass |
| Methyl methacrylate/2-ethylhexyl acrylate/benzyl methacrylate/methacrylic acid copolymer (copolymerization ratio (molar ratio): 55/11.7/4.5/28.8, molecular weight: 100,000, Tg: ca. 70° C.) | 5.83 parts by mass |
| Styrene/acrylic acid copolymer (copolymerization ratio (molar ratio): 63/37, weight average molecular weight: 10,000, Tg: ca. 100° C.) | 13.6 parts by mass |
| Monomer 1 (BPE-500, a trade name, produced by Shin-Nakamura Chemical Co., Ltd.) | 9.1 parts by mass |
| Fluorine polymer | 0.54 part by mass |

The fluorine polymer above was a copolymer of 40 parts of $C_6F_{13}CH_2CH_2OCOCH=CH_2$, 55 parts of $H(OCH(CH_3)CH_2)_7OCOCH=CH_2$ and 5 parts of $H(OCHCH_2)_7OCOCH=CH_2$ having a weight average molecular weight of 30,000 in the form of a 30% by mass methyl ethyl ketone solution (Megafac F780F, a trade name, produced by Dainippon Ink And Chemicals, Inc.).

The coating liquid H1 for a thermoplastic resin layer had a viscosity after removing the solvent at 120° C. of 1,500 Pa·sec.

| Coating Liquid for Intermediate Layer, Formulation P1 | |
|---|---|
| Polyvinyl alcohol (PVA205, a trade name, produced by Kuraray Co., Ltd., saponification degree: 88%, polymerization degree: 550) | 32.2 parts by mass |
| Polyvinylpyrrolidone (K-30, a trade name, produced by ISP Japan Co., Ltd.) | 14.9 parts by mass |
| Distilled water | 524 parts by mass |
| Methanol | 429 parts by mass |

| Composition of Black Resist for Decorative Material, Formulation K1 | |
|---|---|
| K pigment dispersion 1 (having the following composition) | 204.2 parts |
| R pigment dispersion 1 (having the following composition) | 62.36 parts |
| MMPGAc (produced by Daicel Chemical Industries, Ltd.) | 159.1 parts |
| Methyl ethyl ketone (produced by Tonen Chemical Corporation) | 351.3 parts |
| Cyclohexanone | 87.90 parts |

| | |
|---|---|
| Binder 2 (a random copolymer of benzyl methacrylate/methacrylic acid (molar ratio: 78/22, weight average molecular weight: 38,000) | 86.83 parts |
| Propylene glycol monomethyl ether acetate solution of DPHA (dipentaerythritolhexaacrylate, produced by Nippon Kayaku Co., Ltd.) (76% by mass) | 45.24 parts |
| Photopolymerization initiator (having the following structure) | 2.578 parts |
| Phenothiazine (produced by Tokyo Chemical Industry Co., Ltd.) | 0.04744 part |
| Surfactant (Megafac F-780F, a trade name, produced by Dainippon Ink And Chemicals, Inc.) | 0.4849 part |

The black resist K1 for a decorative material had a viscosity after removing the solvent at 100° C. of 10,000 Pa·sec.

Photopolymerization initiator 1 (PM834, produced by Wako Pure Chemical Industries, Ltd., trichloromethyltriazine compound)

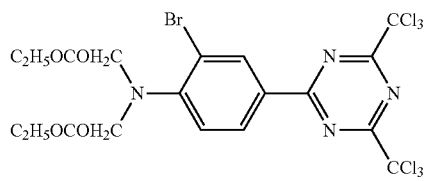

| Composition of K Pigment Dispersion 1 | |
|---|---|
| Carbon black (Nipex 35, a trade name, produced by Degussa AG) | 13.1% by mass |
| Dispersant 1 shown below | 0.65% by mass |
| Binder 1 (a random copolymer of benzyl methacrylate/methacrylic acid (molar ratio: 72/28, weight average molecular weight: (37,000) | 6.72% by mass |
| Propylene glycol monomethyl ether acetate | 79.53% by mass |

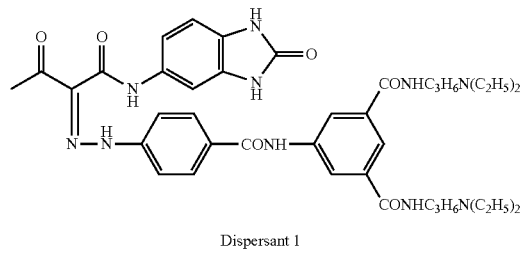

Dispersant 1

| Composition of R Pigment Dispersion 1 | |
|---|---|
| Pigment (C.I. Pigment Red 177) | 18% by mass |
| Binder 1 (a random copolymer of benzyl methacrylate/methacrylic acid (molar ratio: 72/28, weight average molecular weight: 37,000) | 12% by mass |
| Propylene glycol monomethyl ether acetate | 70% by mass |

Formation of Black Resin Film (Decorative Material)

Toughened glass (300 mm×400 mm×0.7 mm) having an opening (diameter: 15 mm) was rinsed with a rotation nylon brush while spraying a glass rinsing liquid controlled to 25° C. by showering thereon for 20 seconds, followed by rinsing with pure water by showering, and then a silane coupling solution (a 0.3% by mass aqueous solution of N-β-(aminoethyl)-γ-aminopropyltrimethoxysilane, KBM603, a trade name, produced by Shin-Etsu Chemical Co., Ltd.) was sprayed by showering thereon for 20 seconds, followed by rinsing with pure water by showering. The substrate was heated to 140° C. for 2 minutes with a substrate preheating equipment. The cover film was removed from the photosensitive film 1 for forming a decorative material, and the surface of the black resist thus exposed by the removal and the surface of the glass substrate having been subjected to the silane coupling treatment obtained above were made in contact with and superimposed on each other, and were laminated by using a laminator (Model Lamic II, produced by Hitachi Industries Co., Ltd.) with the substrate being heated to 140° C., at a rubber roller temperature of 130° C., a linear pressure of 100 N/cm and a conveying speed of 2.2 m/min. Subsequently, the polyethylene terephthalate provisional support was released at the interface to the thermoplastic resin layer to remove the provisional support. After releasing the provisional support, the substrate and an exposure mask (which was a quartz exposure mask having a flame pattern) were set up vertically and exposed patternwise at a distance between the surface of the exposure mask and the black resist for a decorative material of 200 µm and an exposure amount of 70 mJ/cm$^2$ (i line) by using a proximity exposure machine having a super-high pressure mercury lamp (produced by Hitachi High-Tech Electronics Engineering Co., Ltd.).

The photosensitive film was developed by showering a triethanolamine developer liquid (which was obtained by diluting 10 times T-PD2, a trade name, produced by Fujifilm Corporation, containing 30% by mass of triethanolamine, with pure water) at 33° C. for 60 seconds at a flat nozzle pressure of 0.1 MPa, so as to remove the thermoplastic resin layer and the intermediate layer. Subsequently, the liquid was drained by blowing air onto the upper surface of the glass substrate, and then the substrate was rinsed with pure water by showering by spraying pure water by showering for 10 seconds, followed by blowing air thereon to reduce the liquid accumulated on the substrate.

Thereafter, the substrate was developed with a sodium carbonate/potassium hydrogen carbonate developer liquid (which was obtained by diluting 5 times T-CD1, a trade name, produced by Fujifilm Corporation, with pure water) at 32° C. and a shower pressure of 0.1 MPa for 45 seconds, followed by rinsing with pure water.

Subsequently, a surfactant-containing rinsing liquid (which was obtained by diluting 10 times T-SE3, a trade name, produced by Fujifilm Corporation, with pure water) was sprayed thereon by showering at 33° C. for 20 seconds at a cone type nozzle pressure of 0.1 MPa, and the pattern image thus formed was rubbed with a soft nylon rotation brush to remove the residue. Furthermore, super-pure water was sprayed thereon at a pressure of 9.8 MPa with a super-high pressure rinsing nozzle to remove the residue. The resultant was dried.

The substrate was post-exposed in the air at an exposure amount of 1,300 mJ/cm$^2$ from the front surface of the black resist for a decorative material and the substrate side of the black resist for a decorative material, which corresponded to the back surface thereof, and was post-baked at 240° C. for 80 minutes, thereby providing a front plate having a black resin film (decorative material) having an optical density of 3.35 and a thickness of 1.8 µm formed on the silane coupling-treated glass substrate. The resulting black resin film (decorative material) was designated as a black resin film (decorative material) of Example 1.

Evaluation of Thermal Weight Reduction Rate of Black Resin Film (Decorative Material)

The black resin film of Example 1 was scraped off from the silane coupling-treated glass substrate with a razor or the like to prepare a powder specimen. Approximately 6 mg of the resulting powder specimen was measured for a weight reduction rate after heating to 300° C. for 30 minutes with TGA (TG-DTA 6200, produced by Seiko Instruments Inc.

Measurement of Bulk Strength after Heating of Black Resin Film (Decorative Material)

The film strength of the black resin film (decorative material) thus produced was measured by the Sebastian's method.

Specifically, an aluminum pin having a diameter of the bottom surface thereof of 1.6 mm was adhered to the surface of the black resin film (decorative material) of the front plate having the black resin film with an epoxy adhesive. An epoxy adhesive-attached aluminum pin (adhesive-attached aluminum pin 2.7 mm, Model #901106, produced by Quad Group, Inc.) was used herein.

The adhered portion 33 in FIG. 9 of the black resin film and the aluminum pin had a diameter of 1.6 mm, which was the same as the diameter of the bottom surface of the aluminum pin 31.

After curing the epoxy adhesive, the aluminum pin was pulled in a direction that is perpendicular to the black resin film, and the maximum load where the aluminum pin was peeled off was measured.

The results obtained are shown in Table 1 below.

Measurement of Thickness and Evaluation of Taper Angles of Black Resin Film (Decorative Material)

The cross section of the resulting black resin film (decorative material) was photographed with SEM in the just lateral direction at an inclination angle of 0°. A chart was drawn for obtaining taper angles of the black resin film (decorative material) based on the cross sectional photograph of the black resin film (decorative material) according to the following procedures and FIG. 10.

Procedure 1: A contour 21C of the side surface of the black resin film was drawn in the resulting cross sectional photograph of the black resin film (decorative material).

Procedure 2: In the contour formed by the black resin film, a portion 21B of the top surface of the black resin film that was approximately in parallel to the bottom surface of the black resin film was determined, and an extended line $l_B$ thereof was drawn.

Procedure 3: A straight line perpendicular to the straight line $l_B$ was drawn from an arbitrary point B in the portion 21B of the top surface of the black resin film that was approximately in parallel to the bottom surface of the black resin film toward the straight line $l_A$, and the intersection point with the straight line $l_A$ was designated as A. The length of the line segment AB in the perpendicular line was measured to obtain the distance h between the straight line $l_A$ and the straight line $l_B$. The distance was designated as the thickness h of the black resin film shown in Table 1.

Procedure 4: The thickness h was divided into four equal parts, and straight lines $l_1$, $l_2$ and $l_3$ in parallel to the straight line $l_A$ were drawn in this order from the bottom surface of the black resin film.

Procedure 5: The intersecting points of the contour 21C of the side surface of the black resin film and the straight lines $l_1$, $l_2$ and $l_3$ were designated as $C_1$, $C_2$ and $C_3$, respectively, and a straight line $l_{12}$ passing through $C_1$ and $C_2$ and a straight line $l_{23}$ passing through $C_2$ and $C_3$ were drawn.

Figure 11:
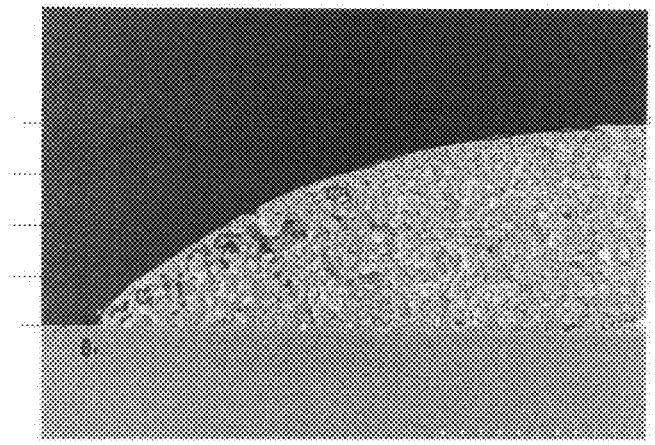
FIG. 11 is an illustrative view showing a result of drawing for obtaining taper angles in an SEM (scanning electron micrograph) of a black resin film (i.e., a decorative material).

FIG. 11 shows the result of drawing for obtaining the taper angles of the black resin film of Example 1 according to the aforementioned procedures. From FIG. 11, the angle $\Theta_1$ that was 90° or less among angles formed between the straight line $l_{12}$ and the extended line $l_A$ of the bottom surface of the black resin film and the angle $\Theta_2$ that was 90° or less among angles formed between the straight line $l_{23}$ and the extended line $l_B$ of the portion of the top surface of the black resin film that was approximately in parallel to the bottom surface of the black resin film were obtained according to the following expressions (1) and (2).

$$\Theta_1 \leq 40° \quad \text{Expression (1)}$$

wherein $\Theta_1$ represents an angle that is 90° or less among angles formed between the straight line $l_{12}$ and the extended line $l_A$ of the bottom surface of the black resin film, in which the straight line $l_{12}$ passes through an intersecting point $C_1$ and an intersecting point $C_2$, the intersecting point $C_1$ is an intersecting point of the side surface of the black resin film and the straight line at a 1/4 height from the surface of the black resin film on the side of the substrate when the height of the black resin film is divided into four equal parts, and the intersecting point $C_2$ is an intersecting point of the side surface of the black resin film and the straight line at a 2/4 height from the surface of the black resin film on the side of the substrate when the height of the black resin film is divided into four equal parts.

$$\Theta_2 \leq 40° \quad \text{Expression (2)}$$

wherein $\Theta_2$ represents an angle that is 90° or less among angles formed between the straight line $l_{23}$ and the extended line $l_B$ of a portion of the top surface of the black resin film that is approximately in parallel to the bottom surface of the black resin film, in which the straight line $l_{23}$ passes through an intersecting point $C_2$ and an intersecting point $C_3$, the intersecting point $C_2$ is an intersecting point of the side surface of the black resin film and the straight line at a 2/4 height from the surface of the black resin film on the side of the substrate when the height of the black resin film is divided into four equal parts, and the intersecting point $C_3$ is an intersecting point of the side surface of the black resin film and the straight line at a 3/4 height from the surface of the black resin film on the side of the substrate when the height of the black resin film is divided into four equal parts.

The taper angles were evaluated from $\Theta_1$ and $\Theta_2$ thus obtained, according to the following standard.

A: The larger angle of $\Theta_2$ and $\Theta_2$ was 35° or less.

B: The larger angle of $\Theta_2$ and $\Theta_2$ exceeded 35° and 40° or less.

C: The larger angle of $\Theta_2$ and $\Theta_2$ exceeded 40°.

The results obtained are shown in Table 1 below.

Formation of First Transparent Electrode Patterns

Formation of Transparent Electrode Layer

The front plate having the decorative material formed thereon was placed in a vacuum chamber, and an ITO thin film having a thickness of 40 nm was formed thereon by using an ITO target having an $SnO_2$ content of 10% by mass (indium/tin: 95/5 (molar ratio)) by DC magnetron sputtering (condition: substrate temperature: 250° C., argon pressure: 0.13 Pa, oxygen pressure: 0.01 Pa), so as to form an ITO thin film having a thickness of 40 nm, thereby providing the front plate having a transparent electrode layer formed thereon. The ITO thin film had a surface resistance of 80Ω per square.

Preparation of Photosensitive Film E1 for Etching

A photosensitive film E1 for etching was obtained in the same manner as in the preparation of the photosensitive film 1 for forming a decorative material except that the black resist K1 was changed to a coating liquid for a photocurable resin layer for etching having the following formulation E1 (the thickness of the photocurable resin layer for etching was 2.0 μm).

| Coating Liquid for Photocurable Resin Layer for Etching, Formulation E1 | |
|---|---|
| Copolymer of methyl methacrylate/styrene/methacrylic acid (copolymerization ratio (% by mass): 31/40/29, mass average molecular weight: 60,000, acid value: 163 mgKOH/g) | 16 parts by mass |
| Monomer 1 (BPE-500, a trade name, produced by Shin-Nakamura Chemical Co., Ltd.) | 5.6 parts by mass |
| Tetraethylene oxide monomethacrylate 0.5 mol adduct of hexamethylene diisocyanate | 7 parts by mass |
| Cyclohexanedimethanol monoacrylate as compound having one polymerizable group in molecule | 2.8 parts by mass |
| 2-Chloro-N-butylacridone | 0.42 part by mass |
| 2,2-Bis (o-chlorophenyl)-4,4',5,5'-tetraphenylbiimidazole | 2.17 parts by mass |
| Malachite Green Oxalate | 0.02 part by mass |
| Leuco Crystal Violet | 0.26 part by mass |
| Phenothiazine | 0.013 part by mass |
| Surfactant (Megafac F-780F, a trade name, produced by Dainippon Ink And Chemicals, Inc.) | 0.03 part by mass |
| Methyl ethyl ketone | 40 parts by mass |
| 1-Methoxy-2-propanol | 20 parts by mass |

The coating liquid E1 for a photocurable resin layer for etching had a viscosity after removing the solvent at 100° C. of 2,500 Pa·sec.

Formation of First Transparent Electrode Patterns

The front plate having the transparent electrode layer was rinsed in the same manner as in the formation of the decorative material, to which the photosensitive film E1 for etching, from which the cover film had been removed, was laminated (substrate temperature: 130° C., rubber roller temperature: 120° C., linear pressure: 100N/cm, conveying speed: 2.2 m/min). After releasing the provisional support, the front plate and an exposure mask (which was a quartz exposure mask having transparent electrode patterns) were exposed patternwise at a distance between the surface of the exposure mask and the photocurable resin layer for etching of 200 μm and an exposure amount of 50 mJ/cm² (i line).

The photosensitive film was then developed with a triethanolamine developer liquid (which was obtained by diluting 10 times T-PD2, a trade name, produced by Fujifilm Corporation, containing 30% by mass of triethanolamine, with pure water) at 25° C. for 100 seconds, then treated with a surfactant-containing rinsing liquid (which was obtained by diluting 10 times T-SD3, a trade name, produced by Fujifilm Corporation, with pure water) at 33° C. for 20 seconds with a rotation brush and a super-high pressure rinsing nozzle to remove the residue, and then post-baked at 130° C. for 30 minutes, thereby providing the front plate having the transparent electrode layer and a photocurable resin layer pattern for etching.

The front plate having formed thereon the transparent electrode layer and the photocurable resin layer pattern for etching was immersed in an ITO etchant (a hydrochloric acid and potassium chloride aqueous solution, liquid temperature: 30° C.) in an etching bath and treated for 100 seconds to dissolve and remove the transparent electrode layer that was exposed but not covered with the photocurable resin layer for etching, thereby providing the front plate having transparent electrode patterns with the photocurable resin layer pattern for etching.

Subsequently, the front plate having the transparent electrode patterns with the photocurable resin layer pattern for etching was immersed in a resist removing liquid (N-methyl-2-pyrrolidone, monoethanolamine and a surfactant (Surfynol 465, a trade name, produced by Air Products and Chemicals, Inc.), liquid temperature: 45° C.) in a resist removing bath and treated for 200 seconds to remove the photocurable resin layer pattern for etching, thereby providing the front plate having the decorative material and the first transparent electrode patterns.

Formation of Insulating Layer

Preparation of Photosensitive Film W1 for Forming Insulating Layer

A photosensitive film W1 for forming an insulating layer was obtained in the same manner as in the preparation of the photosensitive film 1 for forming a decorative material except that the black resist K1 for a decorative material was changed to a coating liquid for a photocurable resin layer for forming an insulating layer having the following formulation W1 (the thickness of the photocurable resin layer for forming an insulating layer was 1.4 μm).

| Coating Liquid for forming Insulating Layer, Formulation W1 | |
|---|---|
| Binder 3 (a 1-methoxy-2-propanol and methyl ethyl ketone solution of a glycidyl methacrylate (d) adduct of a copolymer of cyclohexyl methacrylate (a)/methyl methacrylate (b)/methacrylic acid (c) (composition (% by mass): a/b/c/d = 46/1/10/43, mass average molecular weight: 36,000, acid value: 66 mgKOH/g) (solid content: 45%) | 12.5 parts by mass |
| Propylene glycol monomethyl ether acetate solution of DPHA (dipentaerythritol hexaacrylate, produced by Nippon Kayaku Co., Ltd.) (76% by mass) | 1.4 parts by mass |
| Urethane monomer (NK Oligo UA-32P, a trade name, produced by Shin-Nakamura Chemical Co., Ltd., non-volatile content: 75%, propylene glycol monomethyl ether acetate: 25%) | 0.68 part by mass |
| Pentaerythritol octaacrylate (V #802, a trade name, produced by Osaka Organic Chemical Industry, Ltd.) | 1.8 parts by mass |
| Diethylthioxanthone | 0.17 part by mass |
| 2-(Dimethylamino)-2-[(4-methylphenyl)methyl]-1-4-(4-morpholinyl)phenyl]-1-butanone (Irgacure 379, a trade name, produced by BASF Japan Co., Ltd.) | 0.17 part by mass |
| Dispersant (Solsperse 20000, a trade name, produced by Avecia, Inc.) | 0.19 part by mass |
| Surfactant (Megafac F-780F, a trade name, produced by Dainippon Ink And Chemicals, Inc.) | 0.05 part by mass |
| Methyl ethyl ketone | 23.3 parts by mass |
| MMPGAc (produced by DaicelChemical Industries, Ltd.) | 59.8 parts by mass |

The coating liquid W1 for forming an insulating layer had a viscosity after removing the solvent at 100° C. of 4,000 Pa·sec.

The front plate having the first transparent electrode patterns was rinsed and subjected to the silane coupling treatment in the same manner as in the formation of the decorative material, to which the photosensitive film W1 for forming an insulating layer, from which the cover film had been removed, was laminated (substrate temperature: 100° C., rubber roller temperature: 120° C., linear pressure: 100 N/cm, conveying speed: 2.3 m/min). After releasing the provisional support, the front plate and an exposure mask (which was a quartz exposure mask having a pattern for an insulating layer) were exposed patternwise at a distance between the surface of the exposure mask and the photocurable resin layer for forming an insulating layer of 100 μm and an exposure amount of 30 mJ/cm$^2$ (i line).

The photosensitive film was then developed with a triethanolamine developer liquid (which was obtained by diluting 10 times T-PD2, a trade name, produced by Fujifilm Corporation, containing 30% by mass of triethanolamine, with pure water) at 33° C. for 60 seconds and with a sodium carbonate/sodium hydrogen carbonate developer liquid (which was obtained by diluting 5 times T-CD1, a trade name, produced by Fujifilm Corporation, with pure water) at 25° C. for 50 seconds, then treated with a surfactant-containing rinsing liquid (which was obtained by diluting 10 times T-SD3, a trade name, produced by Fujifilm Corporation, with pure water) at 33° C. for 20 seconds with a rotation brush and a super-high pressure rinsing nozzle to remove the residue, and then post-baked at 230° C. for 60 minutes, thereby providing the front plate having the decorative material, the first transparent electrode patterns and the insulating layer pattern.

Formation of Second Transparent Electrode Patterns
Formation of Transparent Electrode Layer An ITO thin film having a thickness of 80 nm was formed on the front plate having formed thereon the first transparent electrode patterns and the insulating layer pattern by DC magnetron sputtering (condition: substrate temperature: 50° C., argon pressure: 0.13 Pa, oxygen pressure: 0.01 Pa) in the same manner as in the formation of the first transparent electrode patterns, so as to form an ITO thin film having a thickness of 80 nm, thereby providing the front plate having a transparent electrode layer formed thereon. The ITO thin film had a surface resistance of 110Ω per square.

The front plate having formed thereon the first transparent electrode patterns, the insulating layer pattern, the transparent electrode layer and a photocurable resin layer pattern for etching was obtained by using the photosensitive film E1 for etching in the same manner as in the formation of the first transparent electrode patterns (post-baking treatment: 130° C. for 30 minutes).

The etching (30° C. for 50 seconds) and the removal of the photocurable resin layer for etching (45° C. for 200 seconds) were performed in the same manner as in the formation of the first transparent electrode patterns, thereby providing the front plate having the decorative material, the first transparent electrode patterns, the insulating layer pattern and the second transparent electrode patterns.

Formation of Conductive Element Other than from First and Second Transparent Electrode Patterns The front plate having formed thereon the first transparent electrode patterns, the insulating layer patterns and the second transparent electrode patterns was subjected to a DC magnetron sputtering treatment in the same manner as in the formation of the first and second transparent electrode patterns, thereby providing the front plate having an aluminum (Al) thin film having a thickness of 200 nm formed thereon.

The front plate having formed thereon the first transparent electrode patterns, the insulating layer pattern, the second transparent electrode patterns and a photocurable resin layer pattern for etching was obtained by using the photosensitive film E1 for etching in the same manner as in the formation of the first and second transparent electrode patterns (post-baking treatment: 130° C. for 30 minutes).

The etching (30° C. for 50 seconds) and the removal of the photocurable resin layer for etching (45° C. for 200 seconds) were performed in the same manner as in the formation of the first transparent electrode patterns, thereby providing the front plate having the decorative material, the first transparent electrode patterns, the insulating layer pattern, the second transparent electrode patterns, and a conductive pattern other than the first and second transparent electrode patterns.

Formation of Transparent Protective Layer

The front plate having formed thereon until the conductive element other than the first and second transparent electrode patterns was laminated with the photosensitive film W1 for forming an insulating layer, from which the cover film had been removed, and after removing the provisional support, the front plate was subjected to exposure from the front surface thereof without an exposure mask at an exposure amount of 50 mJ/cm$^2$ (i line), development, post-exposure (1,000 mJ/cm$^2$) and post-baking, in the same manner as in the formation of the insulating layer, thereby providing the front plate 1 having laminated thereon an insulating layer (i.e., a transparent protective layer) that covered all the decorative material, the first transparent electrode patterns, the insulating layer pattern, the second transparent electrode patterns and the conductive element other than the first and second transparent electrode patterns.

Production of Image Display Apparatus (Touch-Sensitive Panel)

The front plate 1 thus produced was laminated on a liquid crystal display device produced by the method described in JP-A-2009-47936, and an image display apparatus 1 having the capacitance type input device as a constitutional element was produced by a known method.

Total Evaluation of Front Plate 1 and Image Display Apparatus 1

In all the process steps above, the front plate 1 having the decorative material, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Comparative Example 1

Production of Black Resin Film (Decorative Material)

A front plate having a black resin film (decorative material) having an optical density of 3.35 and a thickness of 1.8 μm formed on the silane coupling-treated glass substrate was obtained in the same manner as in Example 1 by using the photosensitive film 1 for a decorative material formed in the same manner as in Example 1 except that the post-exposure was performed only from the front surface of the black resist for a decorative material. The resulting black resin film (decorative material) was designated as a black resin film (decorative material) of Comparative Example 1.

The resulting black resin film (decorative material) of Comparative Example 1 was evaluated in the same manner as in Example 1. The results are shown in Table 1 below.

Production of Image Display Apparatus (Touch-Sensitive Panel)

A front plate C1 having an insulating layer (transparent protective layer) formed to cover all the decorative material of Comparative Example 1, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Comparative Example 1 formed on the silane coupling-treated glass substrate was used.

The front plate C1 thus produced was laminated on a liquid crystal display device produced by the method described in JP-A-2009-47936, and an image display apparatus C1 of Comparative Example 1 having the capacitance type input device as a constitutional element was produced by a known method.

Total Evaluation of Front Plate and Image Display Apparatus C1

In all the process steps above, the front plate 1 having the decorative material of Comparative Example 1, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Comparative Example 1 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Comparative Example 2

Production of Black Resin Film (Decorative Material)

A front plate having a black resin film (decorative material) having an optical density of 3.35 and a thickness of 1.8 μm formed on the silane coupling-treated glass substrate was obtained in the same manner as in Example 1 by using the photosensitive film 1 for a decorative material formed in the same manner as in Example 1 except that the post-exposure was performed only from the side of the substrate, which corresponded to the back surface of the black resist for a decorative material. The resulting black resin film (decorative material) was designated as a black resin film (decorative material) of Comparative Example 2.

The resulting black resin film (decorative material) of Comparative Example 2 was evaluated in the same manner as in Example 1. The results are shown in Table 1 below.

Production of Image Display Apparatus (Touch-sensitive Panel)

A front plate C2 having an insulating layer (transparent protective layer) formed to cover all the decorative material of Comparative Example 2, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Comparative Example 2 formed on the silane coupling-treated glass substrate was used.

The front plate C2 thus produced was laminated on a liquid crystal display device produced by the method described in JP-A-2009-47936, and an image display apparatus C2 of Comparative Example 2 having the capacitance type input device as a constitutional element was produced by a known method.

Total Evaluation of Front Plate and Image Display Apparatus C2

In all the process steps above, the front plate 1 having the decorative material of Comparative Example 2, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Comparative Example 2 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Comparative Example 3

Production of Black Resin Film (Decorative Material)

A front plate having a black resin film (decorative material) having an optical density of 3.35 and a thickness of 1.8 μm formed on the silane coupling-treated glass substrate was obtained in the same manner as in Example 1 by using the photosensitive film 1 for a decorative material formed in the same manner as in Example 1 except that the post-exposure was not performed. The resulting black resin film (decorative material) was designated as a black resin film (decorative material) of Comparative Example 3.

The resulting black resin film (decorative material) of Comparative Example 3 was evaluated in the same manner as in Example 1. The results are shown in Table 1 below.

Production of Image Display Apparatus (Touch-Sensitive Panel)

A front plate C3 having an insulating layer (transparent protective layer) formed to cover all the decorative material of Comparative Example 3, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Comparative Example 3 formed on the silane coupling-treated glass substrate was used.

The front plate C3 thus produced was laminated on a liquid crystal display device produced by the method described in JP-A-2009-47936, and an image display apparatus C3 of Comparative Example 3 having the capacitance type input device as a constitutional element was produced by a known method.

Total Evaluation of Front Plate and Image Display Apparatus C3

In all the process steps above, the front plate 1 having the decorative material of Comparative Example 3, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Comparative Example 3 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 2

Preparation of Black Resin Film (Decorative Material) of Invention
Preparation of Photosensitive Film 2 for forming Decorative Material A photosensitive film 2 for forming a decorative material was prepared in the same manner as in the preparation of the photosensitive film 1 for a decorative material except that in the preparation of the photosensitive film 1 for a decorative material, the black resist K1 for a decorative material was changed to a black resist K2 for a decorative material that had the same formulation except that the photopolymerization initiator 1 in the formulation of the black resist K1 for a decorative material was changed to a photopolymerization initiator 2 shown below.
Photopolymerization Initiator 2 (Irgacure 379, produced by BASF Japan Co., Ltd., an α-amino-alkylphenone compound)

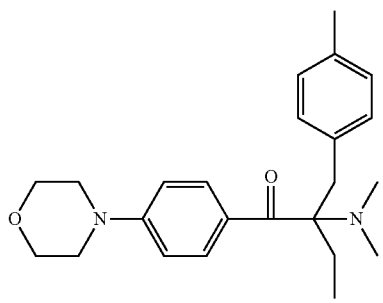 [SMILES: CCC(Cc1ccc(C)cc1)(C(=O)c1ccc(N2CCOCC2)cc1)N(C)C]

Production of Black Resin Film (Decorative Material)

A front plate having a black resin film (decorative material) having an optical density of 3.35 and a thickness of 1.8 μm formed on the silane coupling-treated glass substrate was obtained in the same manner as in Example 1 except that the photosensitive film 2 for a decorative material was used. The resulting black resin film (decorative material) was designated as a black resin film (decorative material) of Example 2.

The resulting black resin film (decorative material) of Example 2 was evaluated in the same manner as in Example 1. The results are shown in Table 1 below.

Production of Image Display Apparatus (Touch-Sensitive Panel)

A front plate 2 having an insulating layer (transparent protective layer) formed to cover all the decorative material of Example 2, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 2 formed on the silane coupling-treated glass substrate was used.

The front plate 2 thus produced was laminated on a liquid crystal display device produced by the method described in JP-A-2009-47936, and an image display apparatus 2 of Example 2 having the capacitance type input device as a constitutional element was produced by a known method.
Total Evaluation of Front Plate and Image Display Apparatus 2

In all the process steps above, the front plate 1 having the decorative material of Example 2, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 2 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 3

A front plate having a black resin film (decorative material) having an optical density of 3.35 and a thickness of 1.8 μm formed on the silane coupling-treated glass substrate was obtained in the same manner as in Example 2 by using the photosensitive film 2 for a decorative material formed in the same manner as in Example 2 except that the post-exposure was performed only from the front surface of the black resist for a decorative material. The resulting black resin film (decorative material) was designated as a black resin film (decorative material) of Example 3.

The resulting black resin film (decorative material) of Example 3 was evaluated in the same manner as in Example 1. The results are shown in Table 1 below.
Production of Image Display Apparatus (Touch-sensitive Panel)

A front plate 3 having an insulating layer (transparent protective layer) formed to cover all the decorative material of Example 3, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 3 formed on the silane coupling-treated glass substrate was used.

The front plate 3 thus produced was laminated on a liquid crystal display device produced by the method described in JP-A-2009-47936, and an image display apparatus 3 of Example 3 having the capacitance type input device as a constitutional element was produced by a known method.
Total Evaluation of Front Plate and Image Display Apparatus 3

In all the process steps above, the front plate 1 having the decorative material of Example 3, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 3 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 4

Production of Black Resin Film (Decorative Material)

A front plate having a black resin film (decorative material) having an optical density of 3.35 and a thickness of 1.8 μm formed on the silane coupling-treated glass substrate was obtained in the same manner as in Example 1 by using the photosensitive film 2 for a decorative material formed in the same manner as in Example 2 except that the post-exposure was performed only from the side of the substrate, which corresponded to the back surface of the black resist for a decorative material. The resulting black resin film (decorative material) was designated as a black resin film (decorative material) of Example 4.

The resulting black resin film (decorative material) of Example 4 was evaluated in the same manner as in Example 1. The results are shown in Table 1 below.
Production of Image Display Apparatus (Touch-Sensitive Panel)

A front plate 4 having an insulating layer (transparent protective layer) formed to cover all the decorative material of Example 4, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 4 formed on the silane coupling-treated glass substrate was used.

The front plate 4 thus produced was laminated on a liquid crystal display device produced by the method described in JP-A-2009-47936, and an image display apparatus 4 of Example 4 having the capacitance type input device as a constitutional element was produced by a known method.
Total Evaluation of Front Plate and Image Display Apparatus 4

In all the process steps above, the front plate 1 having the decorative material of Example 4, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 4 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 5

Preparation of Black Resin Film (Decorative Material) of Invention
Preparation of Photosensitive Film 3 for Forming Decorative Material A photosensitive film 3 for forming a decorative material was prepared in the same manner as in the preparation of the photosensitive film 1 for a decorative material except that in the preparation of the photosensitive film 1 for a decorative material, the black resist K1 for a decorative material was changed to a black resist K3 for a decorative material that had the same formulation except that the photopolymerization initiator 1 in the formulation of the black resist K1 for a decorative material was changed to a photopolymerization initiator 3 shown below.
Photopolymerization Initiator 3 (Irgacure OXE 01, produced by BASF Japan Co., Ltd., an oxime ester compound)

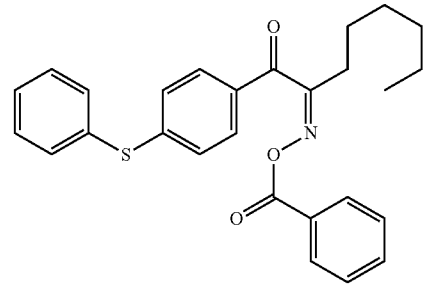 [SMILES: CCCCCC/C(=N/OC(=O)c1ccccc1)C(=O)c1ccc(Sc2ccccc2)cc1]

Production of Black Resin Film (Decorative Material)

A front plate having a black resin film (decorative material) having an optical density of 3.35 and a thickness of 1.8 μm formed on the silane coupling-treated glass substrate was obtained in the same manner as in Example 1 except that the photosensitive film 3 for a decorative material was used. The resulting black resin film (decorative material) was designated as a black resin film (decorative material) of Example 5.

The resulting black resin film (decorative material) of Example 5 was evaluated in the same manner as in Example 1. The results are shown in Table 1 below.
Production of Image Display Apparatus (Touch-sensitive Panel)

A front plate 5 having an insulating layer (transparent protective layer) formed to cover all the decorative material of Example 5, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 5 formed on the silane coupling-treated glass substrate was used.

The front plate 5 thus produced was laminated on a liquid crystal display device produced by the method described in JP-A-2009-47936, and an image display apparatus 5 of Example 5 having the capacitance type input device as a constitutional element was produced by a known method.
Total Evaluation of Front Plate and Image Display Apparatus 5

In all the process steps above, the front plate 1 having the decorative material of Example 5, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 5 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 6

Preparation of Black Resin Film (Decorative Material) of Invention
Preparation of Photosensitive Film 4 for forming Decorative Material A photosensitive film 4 for forming a decorative material was prepared in the same manner as in the preparation of the photosensitive film 1 for a decorative material except that in the preparation of the photosensitive film 1 for a decorative material, the black resist K1 for a decorative material was changed to a black resist K4 for a decorative material that had the same formulation except that the photopolymerization initiator 1 in the formulation of the black resist K1 for a decorative material was changed to a photopolymerization initiator 4 shown below.
Photopolymerization Initiator 4 (Irgacure 184, produced by BASF Japan Co., Ltd., an α-hydroxy-alkylphenone compound)

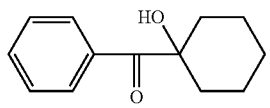 [SMILES: O=C(c1ccccc1)C1(O)CCCCC1]

Production of Black Resin Film (Decorative Material)

A front plate having a black resin film (decorative material) having an optical density of 3.35 and a thickness of 1.8 µm formed on the silane coupling-treated glass substrate was obtained in the same manner as in Example 1 except that the photosensitive film 4 for a decorative material was used. The resulting black resin film (decorative material) was designated as a black resin film (decorative material) of Example 6.

The resulting black resin film (decorative material) of Example 6 was evaluated in the same manner as in Example 1. The results are shown in Table 1 below.
Production of Image Display Apparatus (Touch-Sensitive Panel)

A front plate 6 having an insulating layer (transparent protective layer) formed to cover all the decorative material of Example 6, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 6 formed on the silane coupling-treated glass substrate was used.

The front plate 6 thus produced was laminated on a liquid crystal display device produced by the method described in JP-A-2009-47936, and an image display apparatus 6 of Example 6 having the capacitance type input device as a constitutional element was produced by a known method.
Total Evaluation of Front Plate and Image Display Apparatus 6

In all the process steps above, the front plate 1 having the decorative material of Example 6, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 6 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 7

Preparation of Black Resin Film (Decorative Material) of Invention
Preparation of Photosensitive Film 5 for Forming Decorative Material A photosensitive film 5 for forming a decorative material was prepared in the same manner as in the preparation of the photosensitive film 1 for a decorative material except that in the preparation of the photosensitive film 1 for a decorative material, the dry thickness of the black resist K1 for a decorative material was changed to 2.8 µm.
Production of Black Resin Film (Decorative Material)

A front plate having a black resin film (decorative material) having an optical density of 4.65 and a thickness of 2.5 µm formed on the silane coupling-treated glass substrate was obtained in the same manner as in Example 1 except that the photosensitive film 5 for a decorative material was used. The resulting black resin film (decorative material) was designated as a black resin film (decorative material) of Example 7.

The resulting black resin film (decorative material) of Example 7 was evaluated in the same manner as in Example 1. The results are shown in Table 1 below.

Production of Image Display Apparatus (Touch-Sensitive Panel)

A front plate 7 having an insulating layer (transparent protective layer) formed to cover all the decorative material of Example 7, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 7 formed on the silane coupling-treated glass substrate was used.

The front plate 7 thus produced was laminated on a liquid crystal display device produced by the method described in JP-A-2009-47936, and an image display apparatus 7 of Example 7 having the capacitance type input device as a constitutional element was produced by a known method.

Total Evaluation of Front Plate and Image Display Apparatus 7

In all the process steps above, the front plate 1 having the decorative material of Example 7, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 7 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

Example 8

Preparation of Black Resin Film (Decorative Material) of Invention
Preparation of Photosensitive Film 6 for forming Decorative Material A photosensitive film 6 for forming a decorative material was prepared in the same manner as in the preparation of the photosensitive film 1 for a decorative material except that in the preparation of the photosensitive film 1 for a decorative material, the dry thickness of the black resist K1 for a decorative material was changed to 1.45 µm.

Production of Black Resin Film (Decorative Material)

A front plate having a black resin film (decorative material) having an optical density of 2.42 and a thickness of 1.3 µm formed on the silane coupling-treated glass substrate was obtained in the same manner as in Example 1 except that the photosensitive film 6 for a decorative material was used. The resulting black resin film (decorative material) was designated as a black resin film (decorative material) of Example 8.

The resulting black resin film (decorative material) of Example 8 was evaluated in the same manner as in Example 1. The results are shown in Table 1 below.

Production of Image Display Apparatus (Touch-Sensitive Panel)

A front 8 having an insulating layer (transparent protective layer) formed to cover all the decorative material of Example 8, the first transparent electrode patterns, the insulating layer pattern, the second transparent electrode patterns and the conductive element other than the first and second transparent electrode patterns was obtained in the same manner as in Example 1 except that the front plate having the black resin film (decorative material) of Example 8 formed on the silane coupling-treated glass substrate was used.

The front plate 8 thus produced was laminated on a liquid crystal display device produced by the method described in JP-A-2009-47936, and an image display apparatus 8 of Example 8 having the capacitance type input device as a constitutional element was produced by a known method.

Total Evaluation of Front Plate and Image Display Apparatus 8

In all the process steps above, the front plate 1 having the decorative material of Example 8, the first transparent electrode patterns, the insulating layer pattern, the second transparent electrode patterns, and the conductive element other than the first and second transparent electrode patterns was free of contamination in the opening and the back surface, was easily rinsed, and was free of a problem of contaminating other members.

The decorative material of Example 8 was free of pinhole and was excellent in light shielding property.

The first transparent electrode patterns, the second transparent electrode patterns, and the conductive element other than them each were free of problem in conductivity, and the first transparent electrode patterns and the second transparent electrode patterns were insulated from each other.

Furthermore, the transparent protective layer was free of defects, such as bubbles, and an image display apparatus excellent in display characteristics was obtained.

TABLE 1

| | Black resin film Composition | | | | | Photopolymerization initiator/ ethylenic unsaturated bond-containing compound |
|---|---|---|---|---|---|---|
| | Black pigment | Alkali-soluble polymer compound | Ethylenic unsaturated bond-containing compound | Photopolymerization initiator | | |
| Example 1 | carbon black | binder 1/binder 2 | DPHA | photopolymerization initiator 1 | trichloromethyltriazine compound | 0.075 |
| Comparative Example 1 | carbon black | binder 1/binder 2 | DPHA | photopolymerization initiator 1 | trichloromethyltriazine compound | 0.075 |
| Comparative Example 2 | carbon black | binder 1/binder 2 | DPHA | photopolymerization initiator 1 | trichloromethyltriazine compound | 0.075 |
| Comparative Example 3 | carbon black | binder 1/binder 2 | DPHA | photopolymerization initiator 1 | trichloromethyltriazine compound | 0.075 |

TABLE 1-continued

| | | | | | | |
|---|---|---|---|---|---|---|
| Example 2 | carbon black | binder 1/binder 2 | DPHA | photopolymerization initiator 2 | α-amino-alkylphenone compound | 0.075 |
| Example 3 | carbon black | binder 1/binder 2 | DPHA | photopolymerization initiator 2 | α-amino-alkylphenone compound | 0.075 |
| Example 4 | carbon black | binder 1/binder 2 | DPHA | photopolymerization initiator 2 | α-amino-alkylphenone compound | 0.075 |
| Example 5 | carbon black | binder 1/binder 2 | DPHA | photopolymerization initiator 3 | oxime ester compound | 0.075 |
| Example 6 | carbon black | binder 1/binder 2 | DPHA | photopolymerization initiator 4 | α-hydroxy-alkylphenone compound | 0.075 |
| Example 7 | carbon black | binder 1/binder 2 | DPHA | photopolymerization initiator 2 | α-amino-alkylphenone compound | 0.075 |
| Example 8 | carbon black | binder 1/binder 2 | DPHA | photopolymerization initiator 2 | α-amino-alkylphenone compound | 0.075 |

| | Black resin film | | | | | |
|---|---|---|---|---|---|---|
| | Production method | | | Characteristics | | |
| | Post-exposure (mJ/cm$^2$) | | | | Bulk strength after heating | Shape |
| | Front surface of black resin film | Surface of substrate | Production condition | Weight reduction rate after heating (%) | (N per 1.6 mm in diameter) | Thickness (μm) | Taper angle |
| Example 1 | 1,300 | 1,300 | (B) | 39.2 | 164 | 1.8 | C |
| Comparative Example 1 | 1,300 | 0 | — | 39.4 | 90 | 1.8 | C |
| Comparative Example 2 | 0 | 1,300 | — | 40.3 | 23 | 1.8 | C |
| Comparative Example 3 | 0 | 0 | — | 42.0 | 20 | 1.8 | B |
| Example 2 | 1,300 | 1,300 | (A), (B) | 35.0 | 179 | 1.8 | A |
| Example 3 | 1,300 | 0 | (A) | 36.0 | 172 | 1.8 | A |
| Example 4 | 0 | 1,300 | (A) | 37.6 | 171 | 1.8 | A |
| Example 5 | 1,300 | 1,300 | (A), (B) | 39.4 | 129 | 1.8 | B |
| Example 6 | 1,300 | 1,300 | (A), (B) | 32.0 | 197 | 1.8 | A |
| Example 7 | 1,300 | 1,300 | (A), (B) | 35.0 | 141 | 2.5 | A |
| Example 8 | 1,300 | 1,300 | (A), (B) | 35.0 | 190 | 1.3 | A |

It was understood from Table 1 that the black resin films of the invention obtained by the method for producing a black resin film (decorative material) of the invention that satisfied the condition (A) or (B) defined in the invention had a high bulk strength after heating even when it has a high optical density by using a black pigment. Furthermore, it was also understood that the black resin films of Examples 2 to 8 according to the preferred embodiment of the invention had good taper angles, and the black resin film of Examples 2 to 4 and 6 to 8 according to the preferred embodiment of the invention that satisfied the conditions (A) and (B) defined in the invention had better taper angles.

On the other hand, it was understood from Comparative Examples 1 and 2 that the black resin films of Comparative Examples 1 and 2 produced by the method, in which the post-exposure was performed only from one surface with the use of a trichloromethyltriazine compound as the photopolymerization initiator, and the conditions (A) and (B) defined in the invention were not satisfied, were inferior in bulk strength after heating.

It was understood from Comparative Example 3 that the black resin film (decorative material) produced without post-exposure performed was inferior in bulk strength after heating.

According to the method for producing a capacitance type input device of the invention as described above, a capacitance type input device that was advantageously reduced in thickness and weight was able to be produced with high quality by a convenient process. It was thus understood that the capacitance type input device produced by the production method of the invention and the image display apparatus using the same had high quality.

It was also understood that by using the black resin films of Examples 2 to 8 according to the preferred embodiment of the invention having good taper angles, the resulting capacitance type input device and the image display apparatus using the same were reduced in breakage of circuits that intersected the taper portion, and thus were excellent in the reliability of the touch-sensitive panel.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/057483, filed Mar. 15, 2013, and Japanese Application No. 2012-078946, filed Mar. 30, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

REFERENCE SIGN LIST 1 front plate
2 decorative material
3 first transparent electrode patterns
3a pad portion
3b connecting portion
4 second transparent electrode patterns
5 insulating layer
6 conductive element
7 transparent protective layer
8 opening
10 capacitance type input device
11 toughened glass
12 another conductive element
20 substrate (which may be a front plate or toughened glass)
21 black resin film
21A surface of black resin film on side of substrate
21B portion of top surface opposite to substrate of black resin film that was approximately in parallel to surface of black resin film
21C side surface of black resin film
h height of black resin film
$l_1$ straight line at 1/4 height from surface of black resin film on side of substrate when height of black resin film is divided into four equal parts
$l_2$ straight line at 2/4 height from surface of black resin film on side of substrate when height of black resin film is divided into four equal parts
$l_3$ straight line at 3/4 height from surface of black resin film on side of substrate when height of black resin film is divided into four equal parts
$C_1$ intersecting point of side surface of black resin film and $l_1$
$C_2$ intersecting point of side surface of black resin film and $l_2$
$C_3$ intersecting point of side surface of black resin film and $l_3$
$l_{12}$ straight line passing through $C_1$ and $C_2$
$l_{23}$ straight line passing through $C_2$ and $C_3$
$l_A$ extended line of bottom surface (surface on side of substrate) of black resin film
$l_B$ extended line of portion of top surface (surface opposite to substrate) of black resin film that is approximately in parallel to bottom surface (surface on side of substrate) of black resin film
$\Theta_1$ angle that is 90° or less among angles formed between $l_{12}$ and $l_A$
$\Theta_2$ angle that is 90° or less among angles formed between $l_{23}$ and $l_B$
31 aluminum pin
32 black resin film
33 adhered portion of black resin film and aluminum pin
40 peeling direction of aluminum pin
$D_{31}$ diameter of aluminum pin at adhered portion of black resin film and aluminum pin
C first direction
D second direction

What is claimed is:

1. A method for producing a black resin film, comprising:
applying a photosensitive resin composition containing a black pigment, an alkali-soluble polymer compound, an ethylenic unsaturated bond-containing compound and a photopolymerization initiator, to a substrate,
exposing the photosensitive resin composition on the substrate,
developing the photosensitive resin composition thus exposed, and
subjecting the developed composition to post-exposure, wherein:
the following condition (A) is satisfied:
Condition (A): the photopolymerization initiator is an α-aminoalkylphenone compound or an α-hydroxyalkylphenone compound,
the exposure amount in the post-exposure after the development is 1,300 mJ/cm$^2$ or more in terms of i line, and
the mass ratio of the photopolymerization initiator with respect to the ethylenic unsaturated bond-containing compound in the black resin film is from 0.05 to 0.075.

2. The method for producing a black resin film according to claim 1, wherein the substrate is a transparent substrate.

3. The method for producing a black resin film according to claim 2, wherein the transparent substrate is an insulating transparent substrate.

4. The method for producing a black resin film according to claim 1, which further satisfies the following condition (B):
Condition (B): the post-exposure after the development is performed from both a surface of the photosensitive composition on a side that is in contact with the substrate and a surface thereof on a side that is not in contact with the substrate.

5. The method for producing a black resin film according to claim 1, wherein the photosensitive resin composition is transferred from a photosensitive transfer film, which contains a provisional support having accumulated thereon the photosensitive resin composition, to the substrate.

6. A black resin film that is produced by:
applying a photosensitive resin composition containing a black pigment, an alkali-soluble polymer compound, an ethylenic unsaturated bond-containing compound and a photopolymerization initiator, to a substrate,
exposing the photosensitive resin composition on the substrate,
developing the photosensitive resin composition thus exposed, and
subjecting the developed composition to post-exposure, wherein the following condition (A) is satisfied:
Condition (A): the photopolymerization initiator is an α-aminoalkylphenone compound or an α-hydroxyalkylphenone compound,
the exposure amount in the post-exposure after the development is 1,300 mJ/cm$^2$ or more in terms of i line, and
the mass ratio of the photopolymerization initiator with respect to the ethylenic unsaturated bond-containing compound in the black resin film is from 0.05 to 0.075.

7. A decorative material for a capacitance type input device, comprising a black resin film produced by:
applying a photosensitive resin composition containing a black pigment, an alkali-soluble polymer compound, an ethylenic unsaturated bond-containing compound and a photopolymerization initiator, to a substrate,
exposing the photosensitive resin composition on the substrate,
developing the photosensitive resin composition thus exposed, and subjecting the developed composition to post-exposure, wherein:

the following condition (A) is satisfied:

Condition (A): the photopolymerization initiator is an α-aminoalkylphenone compound or an α-hydroxyalkylphenone compound, the exposure amount in the post-exposure after the development is 1,300 mJ/cm$^2$ or more in terms of i line, and the mass ratio of the photopolymerization initiator with respect to the ethylenic unsaturated bond-containing compound in the black resin film is from 0.05 to 0.075.

8. A capacitance type input device comprising a decorative material for a capacitance type input device, which comprises a black resin film produced by:

applying a photosensitive resin composition containing a black pigment, an alkali-soluble polymer compound, an ethylenic unsaturated bond-containing compound and a photopolymerization initiator, to a substrate, exposing the photosensitive resin composition on the substrate, developing the photosensitive resin composition thus exposed, and subjecting the developed composition to post-exposure, wherein:

the following condition (A) is satisfied:

Condition (A): the photopolymerization initiator is an α-aminoalkylphenone compound or an α-hydroxyalkylphenone compound, the exposure amount in the post-exposure after the development is 1,300 mJ/cm$^2$ or more in terms of i line, and the mass ratio of the photopolymerization initiator with respect to the ethylenic unsaturated bond-containing compound in the black resin film is from 0.05 to 0.075.

9. A method for producing a capacitance type input device comprising a front plate and the following components (1) to (4) on a non-contact surface of the front plate:

(1) a decorative material, (2) plural first transparent electrode patterns that contain plural pad portions that are formed to extend in a first direction and connected through connecting portions, (3) plural second electrode patterns that are electrically insulated from the first transparent electrode patterns, and contain plural pad portions that are formed to extend in a direction intersecting the first direction, and (4) an insulating layer that electrically insulates the first transparent electrode patterns and the second electrode patterns from each other, and wherein the decorative material is produced by:

applying a photosensitive resin composition containing a black pigment, an alkali-soluble polymer compound, an ethylenic unsaturated bond-containing compound and a photopolymerization initiator, to a substrate, exposing the photosensitive resin composition on the substrate, developing the photosensitive resin composition thus exposed, and subjecting the developed composition to post-exposure, wherein:

the following condition (A) is satisfied:

Condition (A): the photopolymerization initiator is an α-aminoalkylphenone compound or an α-hydroxyalkylphenone compound, the exposure amount in the post-exposure after the development is 1,300 mJ/cm$^2$ or more in terms of i line, and the mass ratio of the photopolymerization initiator with respect to the ethylenic unsaturated bond-containing compound in the black resin film is from 0.05 to 0.075.

10. The method for producing a capacitance type input device according to claim 9, wherein the capacitance type input device further contains (5) a conductive element that is other than the first transparent electrode patterns and the second electrode patterns and is electrically connected to at least one of the first transparent electrode patterns and the second electrode patterns.

11. The method for producing a capacitance type input device according to claim 9, wherein the second electrode patterns are transparent electrode patterns.

12. A capacitance type input device comprising a front plate and the following components (1) to (4) on a non-contact surface of the front plate:

(1) a decorative material, (2) plural first transparent electrode patterns that contain plural pad portions that are formed to extend in a first direction and connected through connecting portions, (3) plural second electrode patterns that are electrically insulated from the first transparent electrode patterns, and contain plural pad portions that are formed to extend in a direction intersecting the first direction, and (4) an insulating layer that electrically insulates the first transparent electrode patterns and the second electrode patterns from each other, and wherein the decorative material is produced by:

applying a photosensitive resin composition containing a black pigment, an alkali-soluble polymer compound, an ethylenic unsaturated bond-containing compound and a photopolymerization initiator, to a substrate, exposing the photosensitive resin composition on the substrate, developing the photosensitive resin composition thus exposed, and subjecting the developed composition to post-exposure, wherein:

the following condition (A) is satisfied:

Condition (A): the photopolymerization initiator is an α-aminoalkylphenone compound or an α-hydroxyalkylphenone compound, the exposure amount in the post-exposure after the development is 1,300 mJ/cm$^2$ or more in terms of i line, and the mass ratio of the photopolymerization initiator with respect to the ethylenic unsaturated bond-containing compound in the black resin film is from 0.05 to 0.075.

13. An image display apparatus comprising as a constitutional component a capacitance type input device comprising a decorative material for a capacitance type input device, which comprises a black resin film produced by:

applying a photosensitive resin composition containing a black pigment, an alkali-soluble polymer compound, an ethylenic unsaturated bond-containing compound and a photopolymerization initiator, to a substrate, exposing the photosensitive resin composition on the substrate, developing the photosensitive resin composition thus exposed, and subjecting the developed composition to post-exposure, wherein the following condition (A) is satisfied:

Condition (A): the photopolymerization initiator is an α-aminoalkylphenone compound or an α-hydroxyalkylphenone compound, the exposure amount in the post-exposure after the development is 1,300 mJ/cm$^2$ or more in terms of i line, and the mass ratio of photopolymerization initiator with respect to the ethylenic unsaturated bond-containing compound in the black resin film is from 0.05 to 0.075.

\* \* \* \* \*